US012642525B2

(12) United States Patent

Choi

(10) Patent No.: US 12,642,525 B2

(45) Date of Patent: Jun. 2, 2026

(54) CARTRIDGE FOR SURGICAL INSTRUMENT AND SURGICAL INSTRUMENT INCLUDING THE CARTRIDGE

(71) Applicant: LIVSMED INC., Seongnam-si (KR)

(72) Inventor: Woo Jung Choi, Siheung-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/954,521

(22) Filed: Nov. 20, 2024

(65) Prior Publication Data

US 2025/0160830 A1 May 22, 2025

(30) Foreign Application Priority Data

Nov. 21, 2023 (KR) ......................... 10-2023-0162392

(51) Int. Cl.
*A61B 17/072* (2006.01)
(52) U.S. Cl.
CPC ................... *A61B 17/07207* (2013.01); *A61B 2017/07271* (2013.01)
(58) Field of Classification Search
CPC ........... A61B 2017/07271; A61B 2017/07278; A61B 17/068; A61B 17/07207; A61B 17/072
USPC ........................................... 227/176.1–181.1
See application file for complete search history.

(56) References Cited

U.S. PATENT DOCUMENTS

| | | | |
|---|---|---|---|
| 2006/0278681 A1* | 12/2006 | Viola | ............... A61B 17/00234 227/176.1 |
| 2010/0116867 A1* | 5/2010 | Balbierz | .............. A61B 17/072 227/175.1 |
| 2014/0158741 A1* | 6/2014 | Woodard, Jr. | ....... A61B 17/068 227/175.1 |
| 2017/0027568 A1* | 2/2017 | Scheib | ............. A61B 17/07207 |
| 2021/0186492 A1 | 6/2021 | Shelton, IV et al. | |
| 2022/0313249 A1* | 10/2022 | Eisinger | ............... A61B 17/072 |
| 2023/0301675 A1* | 9/2023 | Seow | ................ A61B 17/0684 |

FOREIGN PATENT DOCUMENTS

| | | | | |
|---|---|---|---|---|
| CN | 116509484 | * | 8/2023 | ....... A61B 17/07207 |
| JP | 2015-061665 A | | 4/2015 | |
| JP | 2020-501776 A | | 1/2020 | |
| WO | WO-2006049852 A2 | * | 5/2006 | ....... A61B 17/00491 |
| WO | WO-2022225367 A1 | * | 10/2022 | ....... A61B 17/07207 |

* cited by examiner

*Primary Examiner* — Linda J. Hodge

(74) *Attorney, Agent, or Firm* — Bridgeway IP Law Group, PLLC; Sang Ho Lee; Hyun Woo Shin

(57) ABSTRACT

A cartridge for a surgical instrument includes an end tool rotatable in at least one direction, the cartridge including a housing, a cover that covers one surface of the housing and has formed thereon a staple hole through which a staple accommodated in the housing is ejected to the outside, a working member arranged inside the housing and configured to move relative to the housing in a first direction that is a lengthwise direction of the housing, a release member on which the staple is arranged, wherein, as the working member moves, the release member moves upward from a lower portion of the housing to an upper portion of the housing to eject the staple to the outside, and an elastic member that is arranged between the housing and the cover, and provides an elastic force in a direction in which the release member is moved downward.

15 Claims, 22 Drawing Sheets

CARTRIDGE FOR SURGICAL INSTRUMENT AND SURGICAL INSTRUMENT INCLUDING THE CARTRIDGE

CROSS-REFERENCE TO RELATED APPLICATION

This application is based on and claims priority under 35 U.S.C. § 119 to Korean Patent Application No. 10-2023-0162392, filed on Nov. 21, 2023, in the Korean Intellectual Property Office, the disclosure of which is incorporated by reference herein in its entirety.

BACKGROUND

1. Field

The present disclosure relates to a surgical instrument, and more particularly, to a surgical instrument that is mountable on a robotic arm or manually operable for use in laparoscopic surgery or various other surgeries.

2. Description of the Related Art

In medical terms, surgery refers to the treatment of diseases by cutting, incising, or manipulating a skin, a mucous membrane, or other tissues by using medical devices. In particular, open surgery for incising and opening the skin of a surgical site to treat, shape, or remove an organ or the like therein causes issues such as bleeding, side effects, patient's pain, or scarring. Therefore, recently, surgery performed by forming a certain hole on a skin and inserting only a medical device, for example, a laparoscopic instrument or a surgical instrument, or surgery using a robot has been spotlighted as an alternative.

The surgical instrument refers to a tool for operating on a surgical site by a doctor manipulating an end tool provided at one end of a shaft passing through a hole drilled in the skin with a certain driving part or a robotic arm. The end tool provided in the surgical instrument performs a rotation motion, a gripping motion, a cutting motion, and the like, through a certain structure.

The above-mentioned background art is technical information possessed by the inventor for the derivation of the present disclosure or acquired during the derivation of the present disclosure, and cannot necessarily be said to be a known technique disclosed to the general public prior to the filing of the present disclosure.

SUMMARY

The present disclosure provides a cartridge capable of automatically retrieving floating a staple that is not fixed to a body tissue, and a surgical instrument including the cartridge, wherein the surgical instrument is mountable on a robotic arm or manually operatable for use in laparoscopic surgery or various other surgeries.

Additional aspects will be set forth in part in the description which follows and, in part, will be apparent from the description, or may be learned by practice of the presented embodiments of the disclosure.

An embodiment of the present disclosure provides a cartridge for a surgical instrument having an end tool rotatable in at least one direction, the cartridge including a housing, a cover that covers one surface of the housing and has formed thereon a staple hole through which a staple accommodated in the housing is ejected to the outside, a working member arranged inside the housing and configured to move relative to the housing in a first direction that is a lengthwise direction of the housing, a release member on which the staple is arranged, wherein, as the working member moves, the release member moves upward from a lower portion of the housing to an upper portion of the housing to eject the staple to the outside, and an elastic member that is arranged between the housing and the cover, and provides an elastic force in a direction in which the release member is moved downward.

In an embodiment of the present disclosure, the elastic member may be fixedly coupled to the release member.

In an embodiment of the present disclosure, when the release member moves upward to the upper portion of the housing, the elastic member may be compressed by the cover or an external structure, and provide the elastic force in the direction in which the release member is moved downward.

In an embodiment of the present disclosure, the elastic member may be fixedly coupled to the cover, and when the release member moves upward to the upper portion of the housing, the elastic member may be compressed by the release member and provide the elastic force in the direction in which the release member is moved downward.

In an embodiment of the present disclosure, one end of the elastic member may be fixedly coupled to the release member, another end of the elastic member may be fixedly coupled to the housing, and when the release member moves upward, the elastic member may provide the elastic force in the direction in which the release member is moved downward.

In an embodiment of the present disclosure, the elastic force provided by the elastic member to the release member may be stronger than a coupling force between the staple and the release member.

In an embodiment of the present disclosure, the elastic member may be formed with the release member as one body.

In an embodiment of the present disclosure, the elastic member may be formed as a separate member from the release member and then coupled to the release member.

In an embodiment of the present disclosure, the working member may include one or more wedges each including a first inclined surface formed such that a height of the first inclined surface on a side of a proximal end of the cartridge is greater than a height of the first inclined surface on a side of a distal end of the cartridge, wherein the proximal end is closer to the connection part than the distal end.

In an embodiment of the present disclosure, the wedge may include a second inclined surface formed from a side of a proximal end of the first inclined surface, such that a height of second inclined surface on a side of a distal end is less than a height of the second inclined surface on the side of the proximal end.

In an embodiment of the present disclosure, when the working member moves toward the distal end of the cartridge in the first direction, the release member may come into contact with the first inclined surface and move upward, and when the working member moves toward the proximal end of the cartridge in the first direction, the release member may come into contact with the second inclined surface and move downward.

In an embodiment of the present disclosure, the release member may include a first contact surface to be in contact with the first inclined surface of the wedge, and a second contact surface to be in contact with the second inclined surface of the wedge, and the first contact surface and the second contact surface may be inclined surfaces formed to have a height on the side of the proximal end of the cartridge being greater than a height on the side of the distal end of the cartridge.

In an embodiment of the present disclosure, as the working member moves toward the distal end of the cartridge in the first direction, the wedge of the working member may sequentially push up a plurality of staples in the cartridge to perform a stapling motion, and simultaneously, a blade may move toward the distal end of the cartridge in the first direction to perform a cutting motion.

In an embodiment of the present disclosure, the staple hole of the cover may form a pocket for accommodating the staple, in an area adjacent to an entrance of the staple hole.

In an embodiment of the present disclosure, the pocket may be configured to have a width greater than a width of the staple hole, and a preset depth.

In an embodiment of the present disclosure, the pocket may be able to accommodate a staple that has failed in stapling and has been released from the release member.

An embodiment of the present disclosure provides a cartridge for a surgical instrument having an end tool rotatable in at least one direction, the cartridge including a housing, a cover that covers one surface of the housing and has formed thereon a staple hole through which a staple accommodated in the housing is ejected to the outside, a working member arranged inside the housing and configured to move relative to the housing in a first direction that is a lengthwise direction of the housing, and a release member on which the staple is arranged, wherein, as the working member moves, the release member moves upward from a lower portion of the housing to an upper portion of the housing to eject the staple to the outside, wherein the release member includes a seating part that supports the staple and on which the staple is seated, and the staple is fixed to the seating part.

In an embodiment of the present disclosure, the seating part may include one or more fastening members, and the fastening member may interfere with the staple while the staple is being seated on the seating part, and fix the staple by using elasticity of the fastening member after the staple is seated on the seating part.

In an embodiment of the present disclosure, an adhesive may be applied between the seating part and the staple such that the staple is fixed to the seating part.

In an embodiment of the present disclosure, the adhesive may be a water-soluble adhesive, and when the staple and the release member come into contact with body tissues, the adhesive may lose its adhesiveness due to moisture in the body tissues.

In an embodiment of the present disclosure, liquid may be applied between the seating part and the staple such that the staple is fixed to the seating part by surface tension of the liquid.

In an embodiment of the present disclosure, the release member may further include a magnetic material, and fix the staple to the seating part by using a magnetic force.

In an embodiment of the present disclosure, the seating part may form a microstructure to fix the staple to the seating part through an adsorption phenomenon.

In an embodiment of the present disclosure, the seating part may form a groove in a lengthwise direction, a lower portion of the staple seated on the seating part may include a curved section laterally curved in at least one area with respect to the lengthwise direction, and when the staple is inserted into the groove of the seating part, elastic deformation may occur in the curved section, and the staple may be fixed to the seating part through a force of the curved section to return to its original state.

In an embodiment of the present disclosure, the staple may include a lower portion in a lengthwise direction, which is seated on the seating part, the seating part may form a groove including a curved section laterally curved in at least one area with respect to the lengthwise direction, and when the staple is inserted into the groove of the seating part, elastic deformation may occur in the lower portion of the staple, and the staple may be fixed to the seating part through a force of the lower portion to return to its original state.

In an embodiment of the present disclosure, the seating part may include a fastening member deformable by an external force, and the release member, while moving upward, may deform the fastening member to be fastened to the staple such that the staple is fixed to the seating part.

In an embodiment of the present disclosure, the staple hole of the cover may have an inclined surface formed such that an inner width of the staple hole becomes narrower toward an upper portion of the staple hole than toward a lower portion of the staple hole.

In an embodiment of the present disclosure, as the release member moves upward, the fastening member may come into contact with the inclined surface and may be deformed by an external force caused by the inclined surface.

In an embodiment of the present disclosure, the staple hole of the cover may form a pocket for accommodating the staple, in an area adjacent to an entrance of the staple hole.

In an embodiment of the present disclosure, the pocket may be configured to have a width greater than a width of the staple hole, and a preset depth.

In an embodiment of the present disclosure, the pocket may be able to accommodate a staple that has failed in stapling and has been released from the release member.

An embodiment of the present disclosure provides a cartridge for a surgical instrument having an end tool rotatable in at least one direction, the cartridge including a housing, a cover that covers one surface of the housing and has formed thereon a staple hole through which a staple accommodated in the housing is ejected to the outside, a working member arranged inside the housing and configured to move relative to the housing in a first direction that is a lengthwise direction of the housing, a release member that accommodates the staple, and as the working member moves, moves upward from a lower portion of the housing to an upper portion of the housing to eject the staple to the outside, and an elastic member that is arranged between the housing and the cover, and provides an elastic force in a direction in which the release member is moved downward, wherein the release member includes a seating part that supports the staple and on which the staple is seated, and the staple is temporarily fixed to the seating part.

Other aspects, features, advantages other than those described above will become apparent from the following drawings, claims, and detailed description of the present disclosure.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 2 is a perspective view illustrating an end tool of the surgical instrument of FIG. 1;

FIG. 17A is a perspective view illustrating a release member and a staple of a cartridge for a surgical instrument according to a second embodiment of the present disclosure;

FIG. 17B is a cross-sectional view illustrating a portion of a cross section of the staple and the release member of FIG. 17A;

DETAILED DESCRIPTION

Figure 1:
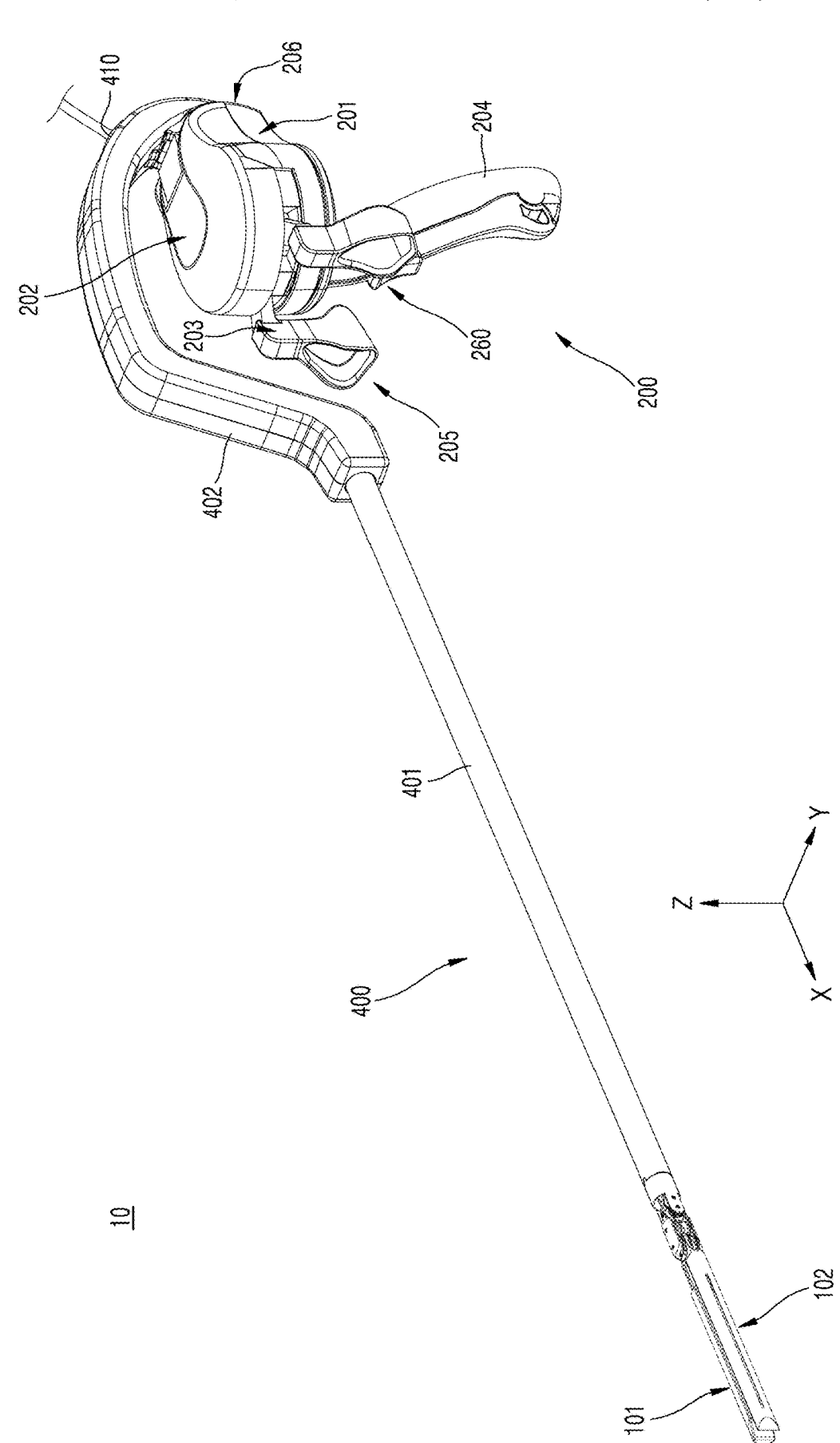
FIG. 1 is a perspective view illustrating a surgical instrument to which a cartridge according to a first embodiment of the present disclosure is applied.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects. As used herein, the term "and/or" includes any and all combinations of one or more of the associated listed items.

Hereinafter, embodiments will be described in detail with reference to the accompanying drawings, and the same or corresponding components will be denoted by the same reference numerals when described with reference to the accompanying drawings, and thus their descriptions that are already provided will be omitted.

As the present embodiments may be variously modified, particular embodiments will be illustrated in the drawings and described in detail in the detailed description. The effects and features of the present embodiments and methods of achieving them will become clear with reference to detail descriptions provided below with the drawings. However, the present embodiments are not limited to the descriptions below, and may be implemented in various forms.

In describing the present disclosure, detailed explanations of the related art are omitted when it is deemed that they may unnecessarily obscure the gist of the present disclosure.

In the following embodiments, the singular expression also includes the plural meaning as long as it is not inconsistent with the context. In the following embodiments, terms such as "first" or "second" may be used to describe various elements, but the elements should not be limited by the terms. These terms are used only to distinguish one element from another.

In the following embodiments, the terms "comprises," "includes," "has", and the like used herein specify the presence of stated features or components, but do not preclude the presence or addition of one or more other features or components.

In the following embodiments, when a unit, region, or component is referred to as being "on" another unit, region, or component, it may be directly or indirectly on the other unit, region, or component, that is, one or more intervening units, regions, or components may be present therebetween.

In the following embodiments, when a component is referred to as being "connected to" or "coupled to" another component, the component may be directly connected to or in direct contact with the other component or intervening components may be present therebetween, unless clearly defined otherwise in the context.

For convenience of description, the magnitude of components in the drawings may be exaggerated or reduced. For example, each component in the drawings is illustrated to have an arbitrary size and thickness for ease of description, and thus the embodiments are not limited to the drawings.

First Embodiment

Figure 2:
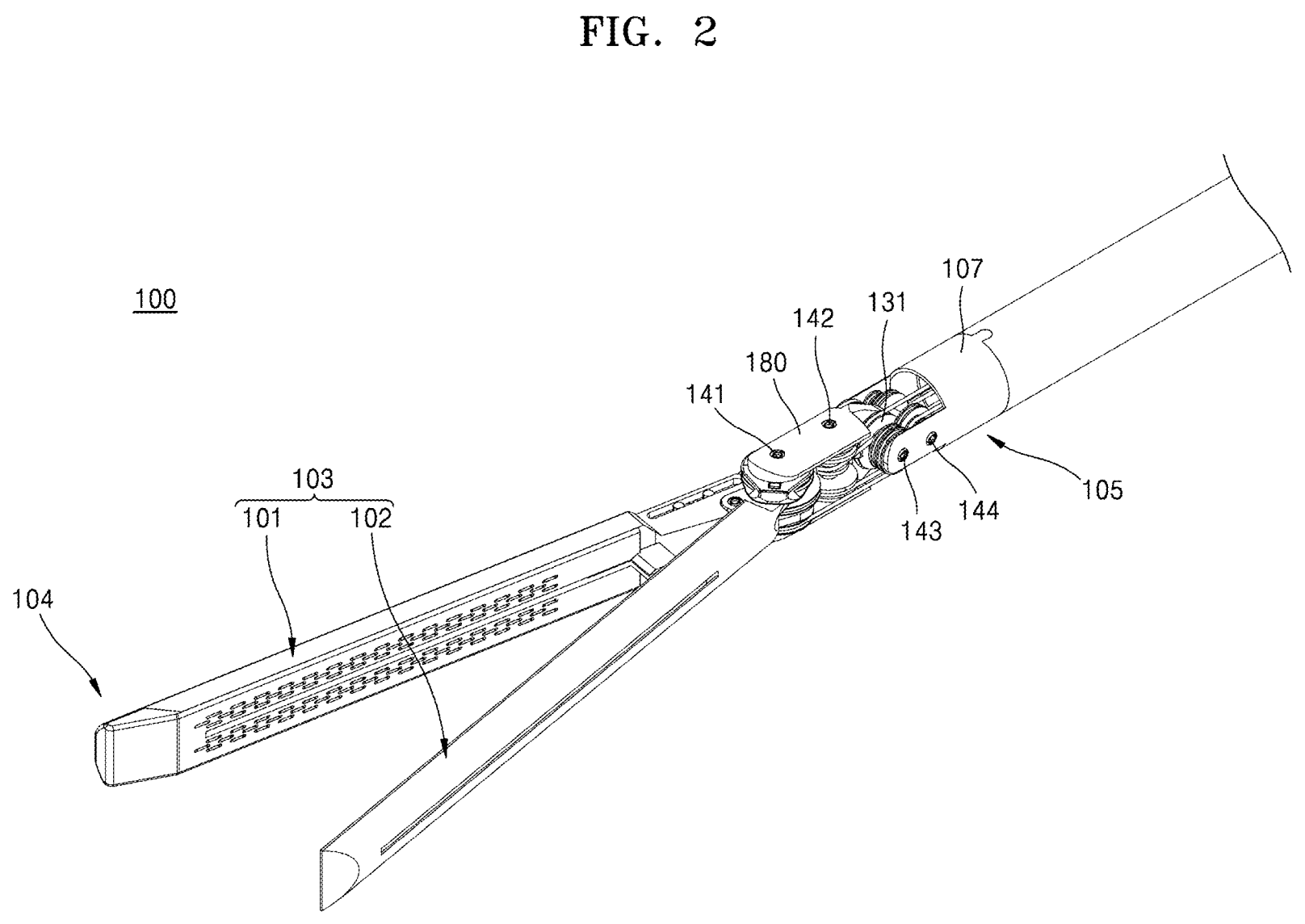

FIG. 1 is a perspective view illustrating a surgical instrument to which a cartridge according to a first embodiment of the present disclosure is applied, and FIG. 2 is a perspective view illustrating an end tool of the surgical instrument of FIG. 1.

Referring to FIG. 1, a surgical instrument 10 according to the first embodiment of the present disclosure includes an end tool 100, a manipulation part 200, a power transmission part (not shown), and a connection part 400.

Here, the connection part 400 may be formed in the shape of a hollow shaft, and one or more wires and electric wires may be accommodated therein. As the manipulation part 200 is coupled to one end of the connection part 400, and the end tool 100 is coupled to the other end, the connection part 400 may serve to connect the manipulation part 200 to the end tool 100.

In addition, the manipulation part 200 may be formed at one end of the connection part 400 and may include an interface which may be directly manipulated by a doctor, for example, an interface in the shape of a pincer, a stick, a lever, etc. When the doctor manipulates the interface, the end tool 100, which is connected to the interface and inserted into the body of a patient, operates in a certain manner to perform a surgery.

Here, although FIG. 1 illustrates that the manipulation part 200 is formed in the shape of a handle that may be rotated while fingers are inserted therein, the present disclosure is not limited thereto, and various types of manipulation parts that may be connected to the end tool 100 to manipulate the end tool 100 may be possible.

The end tool 100 may be formed at the other end of the connection part 400 and may be inserted into a surgical site to perform a motion necessary for surgery. As an example of the end tool 100 as described above, a pair of jaws 103 for performing a grip motion as illustrated in FIG. 2 may be used. However, the concept of the present disclosure is not limited thereto, and various other surgical instruments may be used as the end tool 100. For example, a one-armed cautery may be used as the end tool. As the end tool 100 is connected to the manipulation part 200 by the power transmission part (not shown), the end tool 100 may receive a driving force of the manipulation part 200 through the power transmission part (not shown) to perform motions required for a surgery, such as a grip motion, a cutting motion, a suturing motion, etc.

Here, the end tool 100 of the surgical instrument 10 according to the first embodiment of the present disclosure is formed to be rotatable in two or more directions, and for example, the end tool 100 may be formed to perform a pitch motion around the Y-axis FIG. 1 and simultaneously perform a yaw motion and an actuation motion around the Z-axis of FIG. 1.

In addition, the power transmission part (not shown) may serve to connect the manipulation part 200 to the end tool 100 to transmit the driving force of the manipulation part 200 to the end tool 100, and may include a plurality of wires, pulleys, links, joints, gears, and the like.

In describing the present disclosure, the part close to the user side, that is, the part close to the manipulation part 200 will be referred to as a proximal end, and the part far from the user side, that is, the part close to the end tool 100 will be referred to as a distal end.

Figure 4:
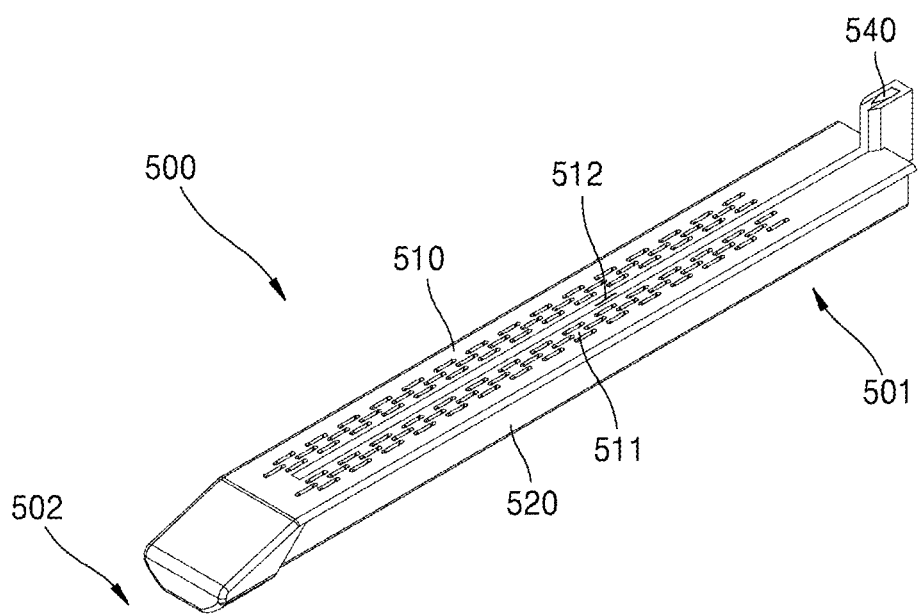
FIG. 4 is an assembled perspective view illustrating the cartridge of FIG. 3.

For example, referring to FIG. 4, the part of a cartridge 500 close to the manipulation part 200 is defined as a proximal end 501 of the cartridge 500, and the part far from the manipulation part 200, that is, the part close to the end of the end tool 100 is defined as a distal end 502 of the cartridge 500. In other words, it may be described that the proximal end 501 of the cartridge 500 is the part close to the connection part 400, and the distal end 502 of the cartridge 500 is the part far from the connection part 400.

The end tool 100 of the first embodiment of the present disclosure includes a pair of jaws for performing a grip motion, that is, a first jaw 101 and a second jaw 102. Here, a component encompassing each of the first jaw 101 and the second jaw 102 or both the first jaw 101 and the second jaw 102 may be referred to as jaws 103.

In addition, the end tool 100 may include pulleys associated with a rotation motion of the first jaw 101 and the second jaw 102.

Here, although the drawings illustrate that the pulleys facing each other are arranged in parallel to each other, the concept of the present disclosure is not limited thereto, and the pulleys may be formed in various positions and sizes suitable for the configuration of the end tool.

In addition, the end tool 100 of the first embodiment the present disclosure may include an end tool hub 180 and a pitch hub 107.

A rotation shaft 141 and a rotation shaft 142 may be inserted through the end tool hub 180, and the end tool hub 180 may accommodate therein at least portions of pulleys that are axially coupled to the rotation shaft 141. In addition, the end tool hub 180 may accommodate therein at least portions of pulleys that are axially coupled to the rotation shaft 142.

In addition, a pulley 131 serving as an end tool pitch pulley may be formed at one end of the end tool hub 180. The pulley 131 may be formed with the end tool hub 180 as one body. That is, a disk-shaped pulley may be formed at one end of the end tool hub 180, and a groove around which a wire may be wound may be formed on an outer circumferential surface of the end tool hub 180. Alternatively, the pulley 131 may be formed as a separate member from the end tool hub 180 and then coupled to the end tool hub 180. A wire (not shown) may be coupled to the pulley 131 serving as an end tool pitch pulley, and a pitch motion may be performed as the pulley 131 rotates around a rotation shaft 143.

The rotation shaft 143 and a rotation shaft 144, which will be described below, may be inserted through the pitch hub 107, and the pitch hub 107 may be axially coupled to the end tool hub 180 (and the pulley 131) by the rotation shaft 143. Thus, the end tool hub 180 and the pulley 131 may be formed to be rotatable around the rotation shaft 143 with respect to the pitch hub 107.

In addition, the pitch hub 107 may accommodate therein at least portions of pulleys that are axially coupled to the rotation shaft 143. In addition, the pitch hub 107 may accommodate therein at least portions of pulleys that are axially coupled to the rotation shaft 144.

Here, the rotation shaft 141 may function as an end tool jaw pulley rotation shaft, the rotation shaft 142 may function as an end tool jaw auxiliary pulley rotation shaft, the rotation shaft 143 may function as an end tool pitch rotation shaft, and the rotation shaft 144 may function as an end tool pitch auxiliary rotation shaft of the end tool 100. One or more pulleys may be fit into each of the rotation shafts 141, 142, 143, and 144.

Here, although not illustrated in the drawings, a pulley serving as an end tool jaw pulley may be fixedly coupled to each of the first jaw 101 and the second jaw 102, to rotate together with the jaw. A yaw motion and an actuation motion of the end tool 100 are performed as the pulleys rotate. That is, when the pulleys of the respective jaws rotate in the same direction around the rotation shaft 141, the yaw motion is performed, and when the pulleys of the respective jaws rotate in opposite directions around the rotation shaft 141, the actuation motion is performed.

Here, the jaw 101 and the pulley may be formed as separate members and then coupled to each other, or may be formed as one body.

Hereinafter, the cartridge 500 of the surgical instrument 10 of FIG. 1 will be described in more detail.

Figure 3:
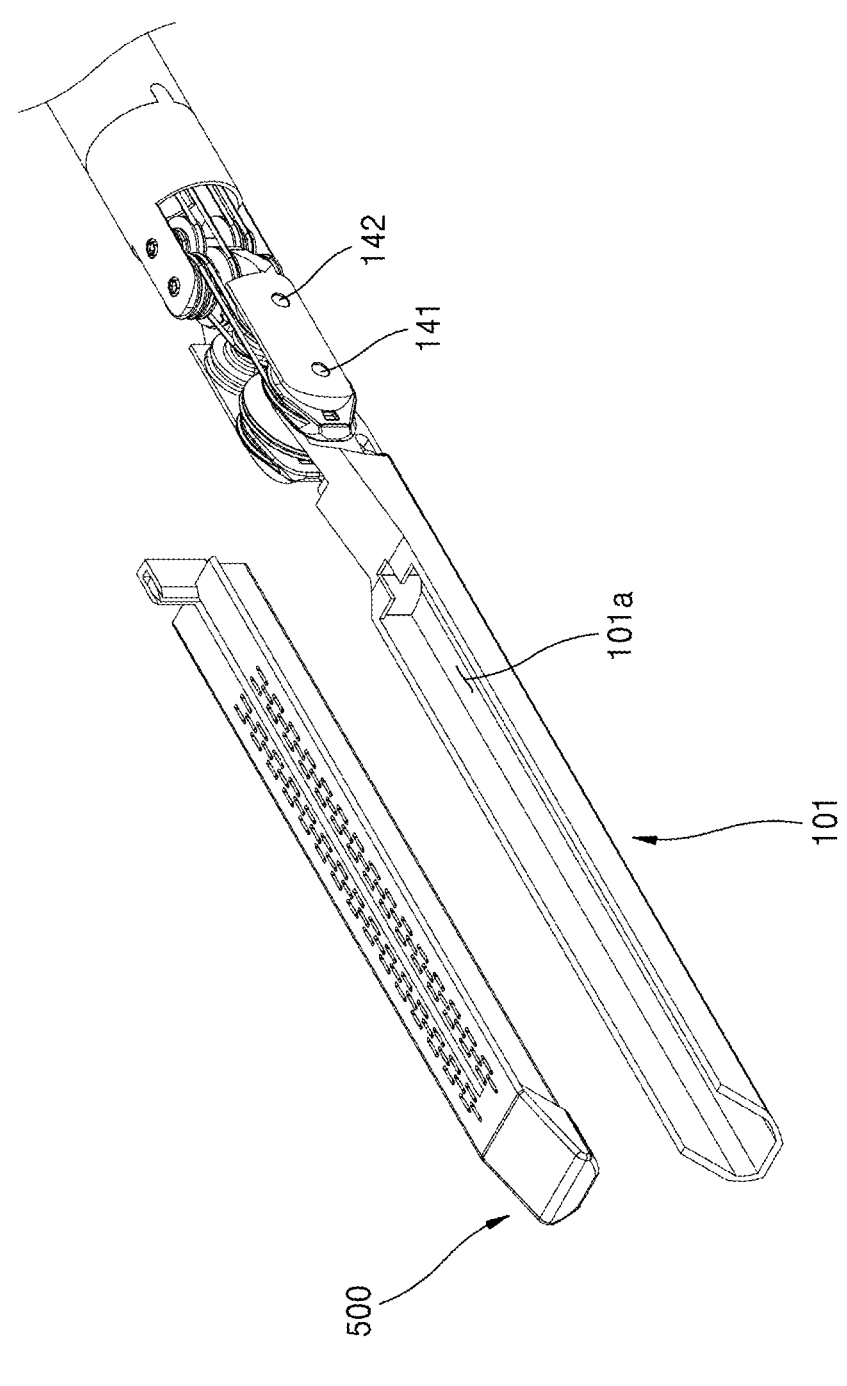
FIG. 3 is a perspective view illustrating a first jaw and a cartridge of the surgical instrument of FIG. 1.
Figure 5:
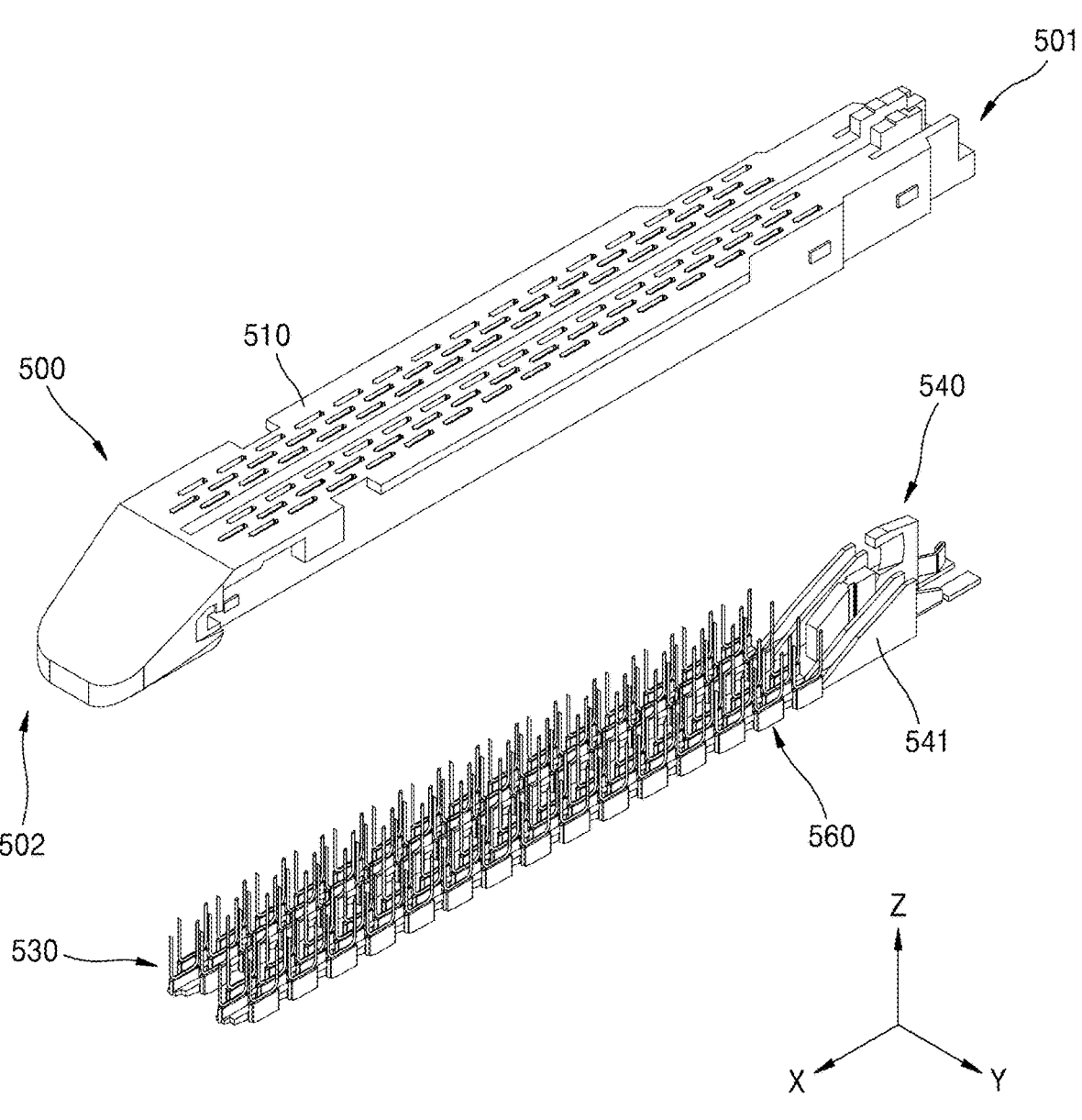
FIG. 5 is an exploded perspective view illustrating some components of the cartridge of FIG. 3.
Figure 6:
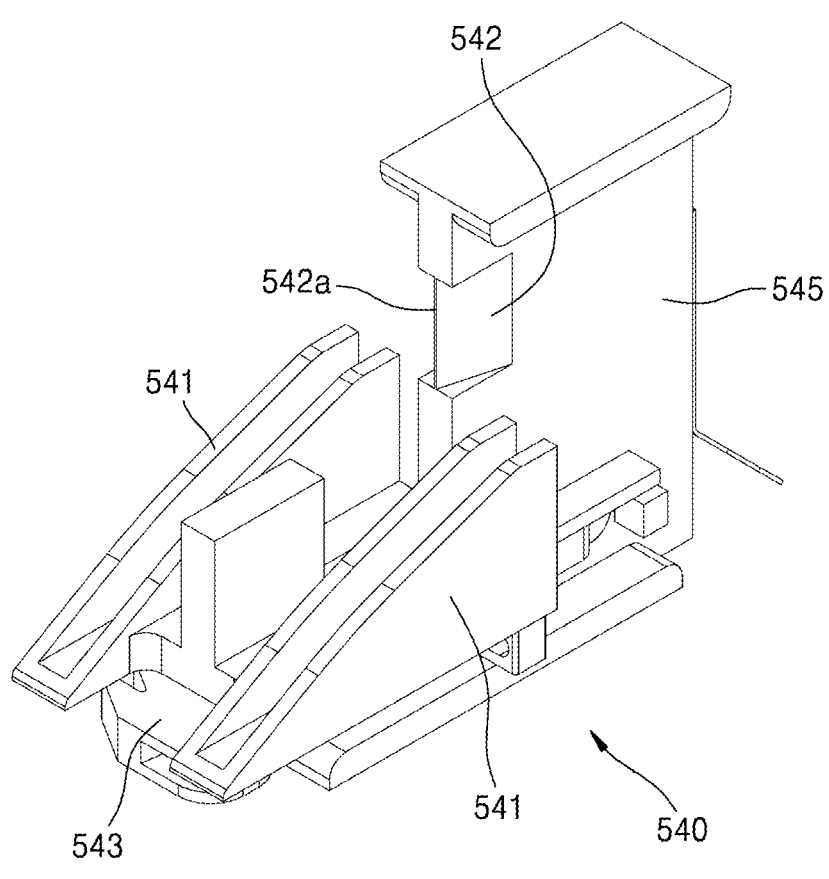
FIG. 6 is a perspective view illustrating a working member of the cartridge of FIG. 3.
Figure 7:
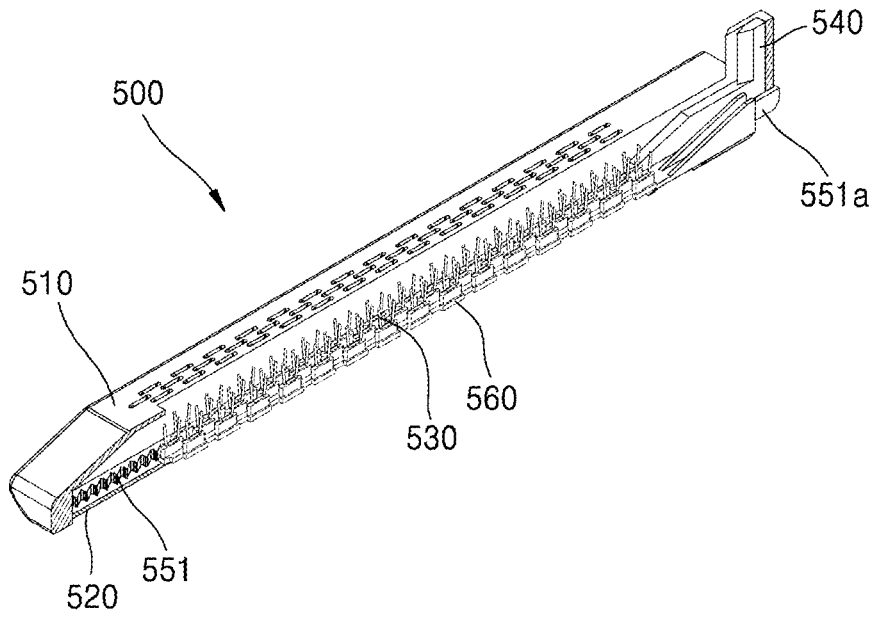
FIG. 7 is a perspective cross-sectional view illustrating the cartridge of FIG. 3.
Figure 8:
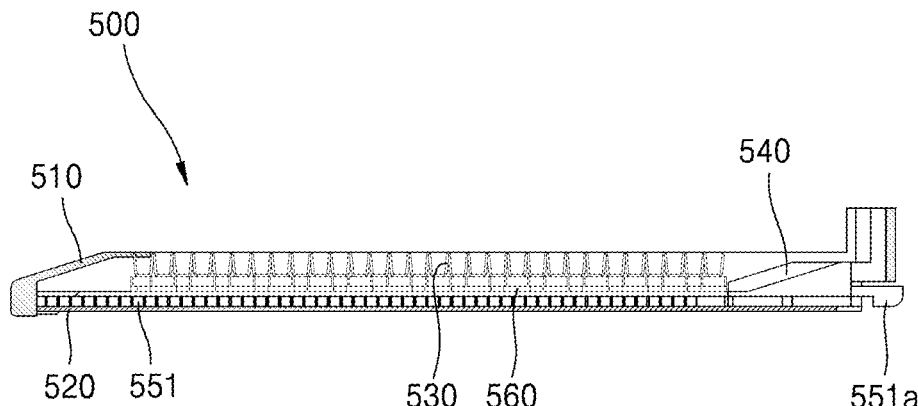
FIG. 8 is a side cross-sectional view illustrating the cartridge of FIG. 3.

FIG. 3 is a perspective view illustrating a first jaw and a cartridge of the surgical instrument of FIG. 1. FIG. 4 is a assembled perspective view illustrating the cartridge of FIG. 3, and FIG. 5 is an exploded perspective view illustrating some components of the cartridge of FIG. 3. FIG. 6 is a perspective view illustrating a working member of the cartridge of FIG. 3, and FIG. 7 is a perspective cross-sectional view illustrating the cartridge of FIG. 3. FIG. 8 is a side cross-sectional view illustrating the cartridge of FIG.

Figure 9A:
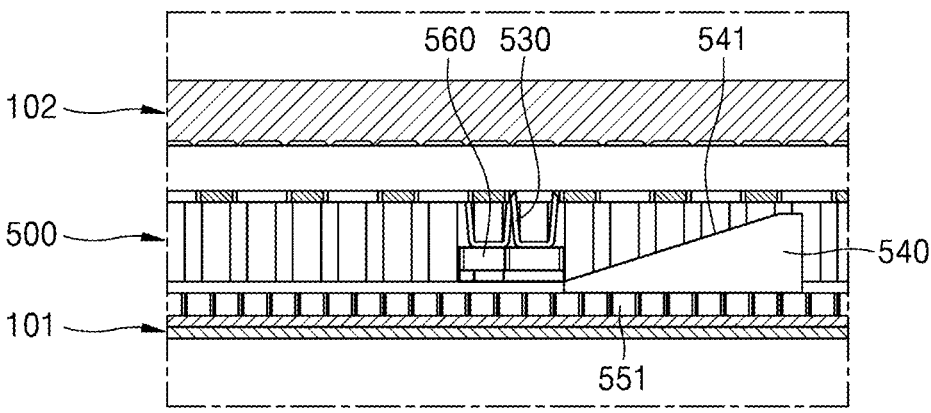
FIGS. 9A to 9C are side cross-sectional views illustrating an overall stapling motion of the cartridge of FIG. 8.
Figure 9B:
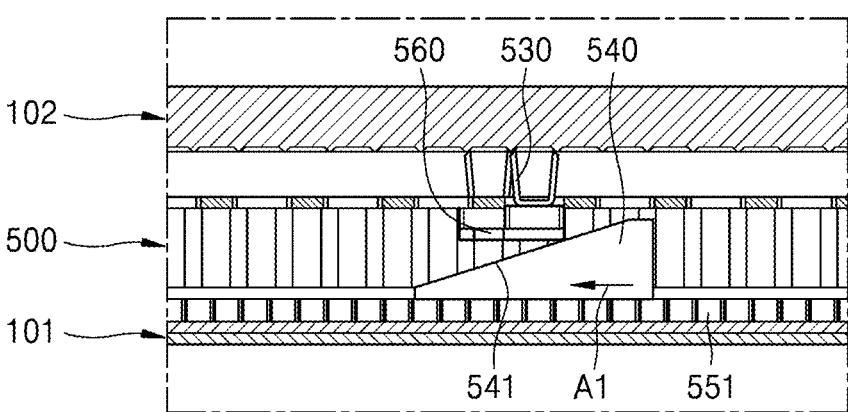
Figure 9C:
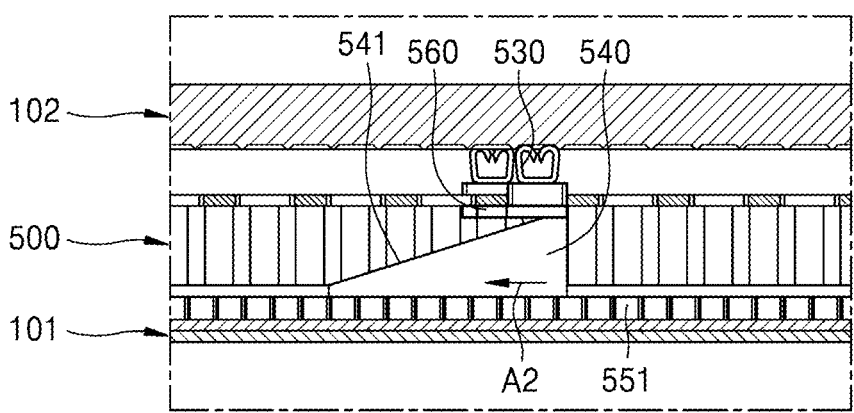

3, and FIGS. 9A and 9C are side cross-sectional views illustrating an overall stapling motion of the cartridge of FIG. 8.

Referring to FIGS. 3 to 9C and the like, the cartridge 500 is formed to be mountable to and dismountable from the first jaw 101, and includes therein a plurality of staples 530 and a blade 542 so as to perform suturing and cutting of tissue. Here, the cartridge 500 may include a cover 510, a housing 520, the staples 530, a release member 560, a working member 540, and a reciprocating assembly (not shown).

The housing 520 forms the exterior of the cartridge 500, and may be formed entirely in the shape of a hollow box with one surface (an upper surface) removed, to accommodate therein the reciprocating assembly (not shown), the working member 540, and the staples 530. Here, the housing 520 may be formed in an approximately 'U'-shape in cross section.

The cover 510 is formed to cover an upper portion of the housing 520. Staple holes 511 through which the plurality of staples 530 may be ejected to the outside may be formed in the cover 510. As the staples 530, which are accommodated in the housing 520 before a stapling operation, are pushed up by the working member 540 during a stapling motion, and then pass through the staple holes 511 of the cover 510 to be released to the outside of the cartridge 500, stapling is performed.

In addition, a slit 512 may be formed in the cover 510 along the lengthwise direction of the cover 510. The blade 542 of the working member 540 may protrude out of the cartridge 500 through the slit 512. As the blade 542 of the working member 540 passes along the slit 512, stapled tissue may be cut.

The plurality of staples 530 may be arranged inside the housing 520. As the working member 540, which will be described below, linearly moves in one direction, the plurality of staples 530 may be sequentially pushed up from the inside of the housing 520 to the outside, thereby performing suturing, that is, stapling. Here, the material of the staples 530 may include titanium, stainless steel, etc.

In addition, the release member 560 may be further arranged between the housing 520 and the staple 530. In other words, it may also be described that the staple 530 is arranged on the release member 560. In this case, the working member 540 may linearly move in one direction to push up the release member 560, and the release member 560 may push up the staples 530.

This may include a case in which the working member 540 directly pushes up the staples 530, and a case in which the working member 540 pushes up the release member 560 such that the release member 560 pushes up the staples 530 (i.e., a case in which the working member 540 indirectly pushes up the staples 530), and thus, it may be described that the working member 540 pushes up the staples 530.

In addition, there may be various methods by which the working member 540 linearly moves, that is, methods by which the working member 540 moves in one direction from the proximal end of a jaw to the distal end.

For example, the working member 540 may linearly move by a reciprocating member (not shown) that transforms a rotation motion of a pulley to a linear reciprocating motion of the reciprocating member (not shown) so as to perform a linear reciprocating motion. Alternatively, a wire may be directly fixed to the working member 540 such that the working member 540 linearly moves through a structure using the pulley and the wire. However, the technical idea of the present disclosure is not limited thereto, and of course, various mechanisms for linearly moving the working member 540 may be used. Hereinafter, for convenience of description, an example will be described in which the working member 540 is linearly moved by using the reciprocating member (not shown) described above.

The working member 540 may be arranged inside the housing 520. The working member 540 may be formed to be in contact with the reciprocating member (not shown), so as to linearly move in one direction according to a linear reciprocating motion of the reciprocating member (not shown). In other words, the working member 540 interacts with the reciprocating member (not shown) to perform stapling and cutting while moving in the extension direction of the connection part 400.

The working member 540 may include a wedge 541, the blade 542, a ratchet member 543, and a main body 545.

The main body 545 may be formed in the shape of a long quadrangular column and forms a base of the working member 540.

The wedge 541 may be formed on at least one side of the main body 545, and may be combined with the main body 545 or formed with the main body 545 as one body. In addition, the wedge 541 may be formed to have a certain inclined surface. That is, the wedge 541 may be formed to be inclined to a certain degree in the extension direction of the connection part 400. In other words, the wedge 541 may be formed such that the height of the wedge 541 on the side of the proximal end 501 is higher than the height of the wedge 541 on the side of the distal end 502. The drawings illustrate that two wedges 541 are formed on both sides of the main body 545, but the concept of the present disclosure is not limited thereto, and the number and shape of wedges 541 may vary depending on the shape of the staple 530 or the release member 560 that is in contact with the wedge 541.

Figure 10:
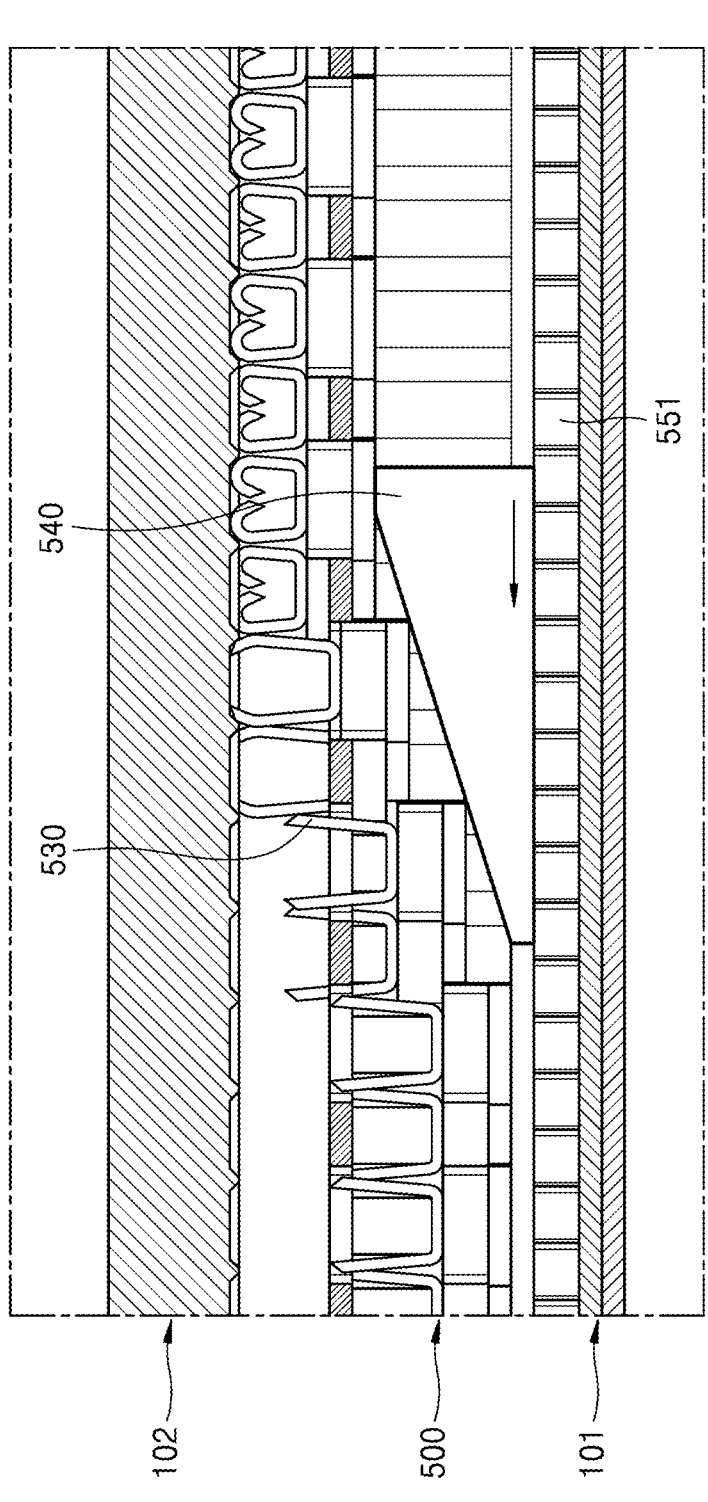
FIG. 10 is a side cross-sectional view illustrating an overall stapling motion of the cartridge of FIG. 8.

The wedge 541 may be formed to be in sequential contact with the release members 560 or the plurality of staples 530 and thus may serve to sequentially push up the staples 530. As illustrated in FIG. 10 and the like to be described below, the working member 540 may serve to, while moving toward the distal end 502, sequentially push up the staples 530 to be released from the cartridge 500.

The blade 542 may be formed on one side of the wedge 541, more specifically, on the side close to the proximal end 501. In one area of the blade 542, a sharp edge part 542a may be formed to cut tissue. At least a portion of the edge part 542a may be withdrawn to the outside from the first jaw 101 and the cartridge 500, so as to cut tissue arranged between the first jaw 101 and the second jaw 102. The edge part 542a of the blade 542 may be always withdrawn to the outside from the first jaw 101. Alternatively, the edge part 542a of the blade 542 may be normally accommodated in the first jaw 101 or the cartridge 500, and only when the working member 540 moves in the longitudinal direction, the edge part 542a may be withdrawn to the outside from the first jaw 101.

FIGS. 9A to 9C are side cross-sectional views illustrating each section of a stapling motion of the cartridge of FIG. 8, and FIG. 10 is a side cross-sectional view illustrating an overall stapling motion of the cartridge of FIG. 8.

In the state illustrated in FIG. 9A, as the working member 540 moves in the direction of arrow A1 in FIG. 9B, the wedge 541 of the working member 540 pushes up the release member 560, and the release member 560 pushes up the lower side of the staple 530. This causes the staple 530 to be ejected from the first jaw 101 and the cartridge 500.

In this state, when the working member 540 moves further in the direction of arrow A2 in FIG. 9C, the ejected staple 530 is continuously pushed up by the working member 540 while being in contact with an anvil (not shown) of the second jaw 102, both ends of the staple 530 are bent, and thus, stapling is performed.

As the above motions are continuously performed, stapling is sequentially performed from the staple 530 on the side of the proximal end 501 to the staple 530 on the side of the distal end 502 among the plurality of staples 530, as illustrated in FIG. 10.

In summary, in the surgical instrument 10 according to an embodiment of the present disclosure, as the working member 540 moves toward the distal end 502 of the cartridge 500, the working member 540 ejects the staples 530 from the cartridge 500, and simultaneously, the blade 542 of the working member 540 moves toward the distal end 502 of the cartridge 500. Here, it may be described that, the surgical instrument 10 according to an embodiment of the present disclosure simultaneously performs suturing and cutting of a body tissue interposed between the first jaw 101 and the second jaw 102.

In addition, during a stapling procedure, not all staples 530 may be fixed to body tissues and some of them may float inside the body. For example, when the starting point of the staple arrangement is located in a part where tissue is not placed, initial few staples 530 may not be fixed to the tissue and may freely float when stapling begins.

It is generally recommended to remove such staples that are not fixed, but this process is cumbersome and there are problems in that the staples may not be completely retrieved.

Thus, there is a need for a system for automatically retrieving staples that are not fixed to tissue in a stapling procedure.

The present disclosure is designed to resolve such problems and provides a cartridge for a surgical instrument capable of preventing the occurrence of floating staples or retrieving floating staples by using several mechanisms to be described below.

Hereinafter, a release member 560 and the staple 530 of the cartridge 500 according to a first embodiment of the present disclosure will be described.

Figure 11:
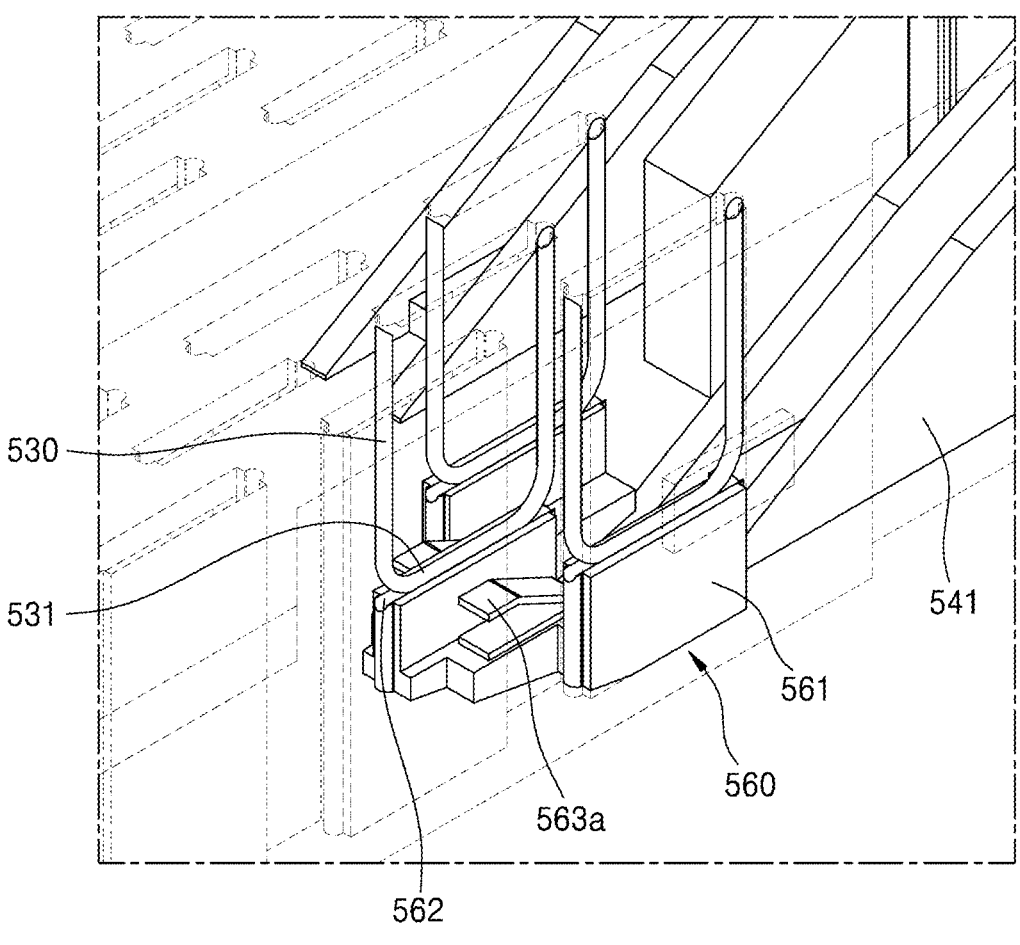
FIG. 11 is an enlarged perspective view illustrating a release member and a staple of FIG. 5.
Figure 12:
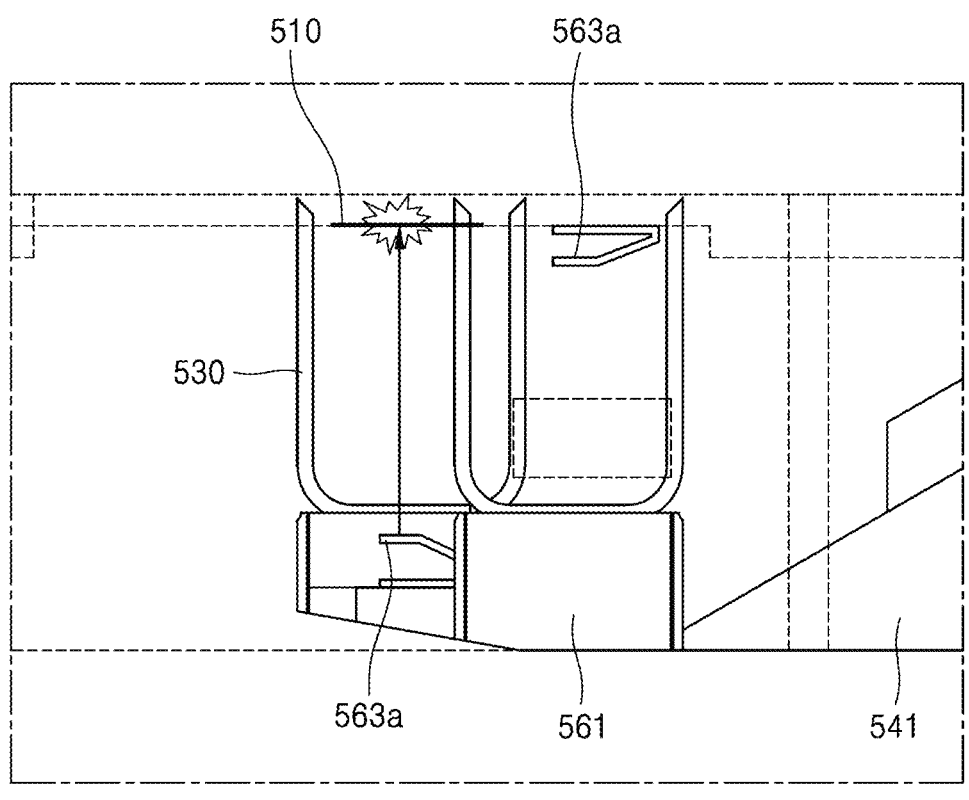
FIG. 12 is a side view of the release member and the staple of FIG. 11.

FIG. 11 is an enlarged perspective view illustrating the release member and the staple of FIG. 5, and FIG. 12 is a side view of the release member and the staple of FIG. 11.

Referring to FIGS. 11 and 12, the cartridge 500 according to the first embodiment of the present disclosure may include the wedge 541 of the working member 540, the release member 560, and the staple 530.

The release member 560 may include a support 561 that accommodates or supports the staple 530. The support 561 may be formed in the shape of a long quadrangular column, and a seating part 562 on which the staple 530 may be seated may be formed on the support 561. In addition, the seating part 562 may be formed in the shape of a groove in the longitudinal direction, and may be formed to accommodate at least a portion of the staple 530.

In addition, one support 561 and one staple 530 may be provided in one release member 560, or a plurality of supports 561 and staples 530 may be provided in one release member 560. For example, as illustrated in FIG. 11, the release member 560 may be formed as one body by connecting the lower ends of three supports 561.

In addition, the cartridge 500 according to the first embodiment of the present disclosure may include an elastic member 563a. Here, the elastic member 563a is interposed between the housing 520 and the cover 510, and may provide an elastic force in a direction to move the release member 560 downward. In other words, a device may be provided to move downward again the release member 560 that moves upward inside the housing 520 as the wedge 541 moves.

In detail, the elastic member 563a may be fixedly coupled to the release member 560. When the release member 560 moves upward to an upper portion of the housing 520, the elastic member 563a may be compressed by the cover 510 or an external structure and thus provide an elastic force in a direction to move the release member 560 downward. That is, as the release member 560 pushed up by the wedge 541 approaches the cover 510 or the external structure, the elastic member 563a coupled to the release member 560 may come into contact with the cover 510 or the external structure and thus be compressed. At this time, the release member 560 may be pushed up enough to eject the staple 530 to the outside of the cover through the staple hole 511.

Accordingly, when the wedge 541, which pushes up the release member 560, moves toward the distal end and passes through the release member 560, the force pushing up the release member 560 may be removed, and thus, the release member 560 may be moved downward by the elastic force of the elastic member 563a. In addition, the staple 530 that is not fixed to a body tissue may be inserted back into the housing 520 together with the release member 560.

Here, the elastic member 563a may be formed in the shape of a plate spring, such that one end of the elastic member 563a is coupled to one side of the release member 560, and the other end is spaced apart from the one end and formed to be elastically deformable by a pressure. Here, the elastic member 563a is described above as having the shape of a plate spring as an example, but may have other various shapes capable of providing an elastic force, such as a coil spring or a disk spring.

As another example, the elastic member 563a may be fixedly coupled to the cover 510, and when the release member 560 moves upward to an upper portion of the housing 520, the elastic member 563a may be compressed by the release member 560 and thus provide an elastic force to move the release member 560 downward. That is, as the release member 560 pushed up by the wedge 541 approaches the cover 510, the elastic member 563a coupled to the lower surface of the cover 510 may come into contact with the release member 560 and thus be compressed. At this time, the release member 560 may be pushed up enough to eject the staple 530 to the outside of the cover through the staple hole 511.

Similarly, the elastic member 563a may be formed in the shape of a plate spring, such that one end of the elastic member 563a is coupled to the lower surface of the cover 510, and the other end is spaced apart from the one end and formed to be elastically deformable by a pressure. Here, the elastic member 563a is described above as having the shape of a plate spring as an example, but may have other various shapes capable of providing an elastic force, such as a coil spring or a disk spring.

In a case in which the elastic member 563a is fixed to the release member 560, the cover 510 or the like, the elastic member 563a is compressed and deformed to provide an elastic force to the release member 560. At this time, the release member 560 may move downward to a certain degree such that the release member 560 returns to its initial position, or to a minimum degree such that the staple 530 is released from the release member 560.

Here, an example in which the elastic member 563a is fixed to the release member 560 and an example in which the elastic member 563a is fixed to the cover 510 are described above, but the elastic member 563a may be interposed anywhere between the cartridge 500 and the release member 560. In detail, the elastic member 563*a* may be interposed between the housing 520 and the release member 560 of the cartridge 500.

First Modification of First Embodiment

Hereinafter, the release member 560 and the staple 530 of the cartridge 500 according to a first modification of the first embodiment of the present disclosure will be described. Here, the cartridge according to the first modification of the first embodiment of the present disclosure is different from the cartridge (see 500 of FIG. 3 and the like) according to the first embodiment of the present disclosure described above, in the coupling position of the elastic member and the force applied by the elastic member.

Figure 13:
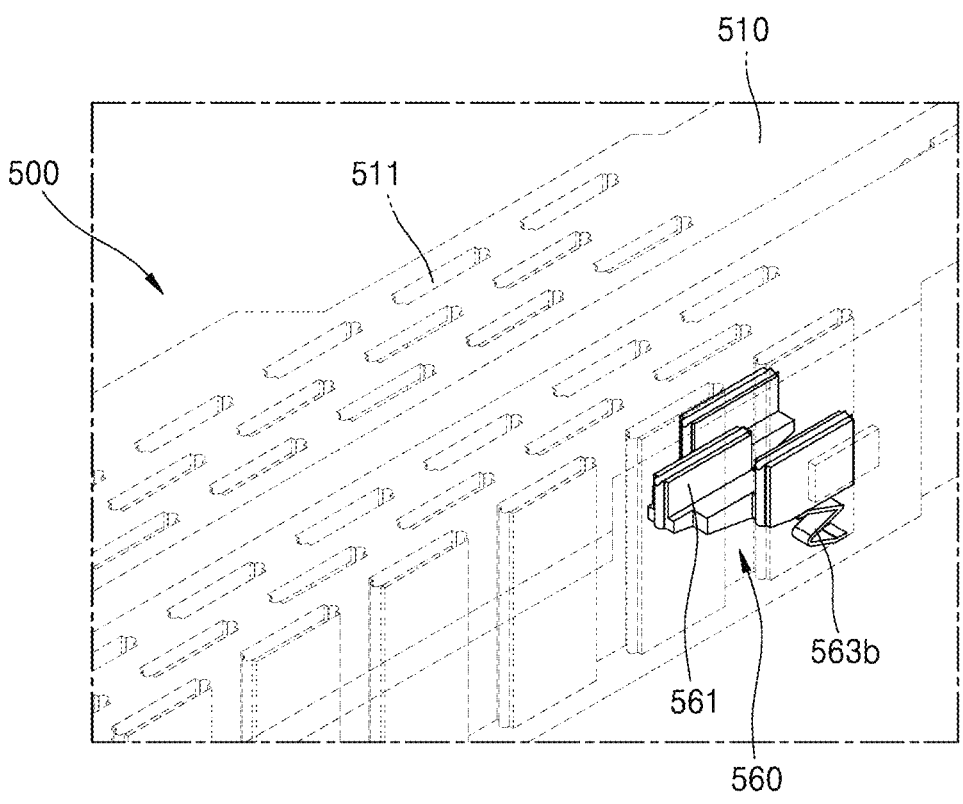
FIG. 13 is an enlarged perspective view illustrating a cartridge and a release member of a surgical instrument according to a first modification of the first embodiment of the present disclosure.

FIG. 13 is an enlarged perspective view illustrating a cartridge and a release member of a surgical instrument according to the first modification of the first embodiment of the present disclosure.

Referring to FIG. 13, the cartridge 500 according to the first modification of the first embodiment of the present disclosure may include the release member 560. In addition, although not illustrated in the drawing, the cartridge 500 may include the wedge 541 of the working member 540, and the staple 530. The working member 540, the wedge 541, the staple 530, and the like are substantially the same as those of the cartridge 500 according to the first embodiment of the present disclosure, and thus, detailed descriptions thereof will be omitted.

The release member 560 of the cartridge 500 according to the first modification of the first embodiment of the present disclosure may include an elastic member 563*b* that is interposed between the housing 520 and the cover 510, and provides an elastic force in a direction to move the release member 560 downward.

Here, one end of the elastic member 563*b* may be fixedly coupled to the release member 560, and the other end of the elastic member 563*b* may be fixedly coupled to the housing 520, such that, when the release member 560 moves upward, the elastic member 563*b* provides an elastic force in a direction to move the release member 560 downward.

In detail, when the release member 560 moves upward to an upper portion of the housing 520, the elastic member 563*b* may be elastically deformed to apply a tensile force in a direction to move the release member 560 downward. That is, as the release member 560 is pushed up by the wedge 541 toward an upper portion of the housing 520, that is, toward the cover 510, the elastic member 563*b* coupled to the release member 560 may be stretched. At this time, the release member 560 may be pushed up enough to eject the staple 530 to the outside of the cover through the staple hole 511.

Accordingly, when the wedge 541, which pushes up the release member 560, moves toward the distal end and passes through the release member 560, the force pushing up the release member 560 may be removed, and thus, the release member 560 may be moved downward by the tensile force of the elastic member 563*b*. In addition, the staple 530 that is not fixed to a body tissue may be inserted back into the housing 520 together with the release member 560.

Here, the elastic member 563*b* may include a tension spring, a plate spring, or the like. In addition, the elastic member 563*b* may be formed as a separate member from the release member 560 and then coupled to the release member 560. Alternatively, the elastic member 563*b* may be formed with the release member 560 as one body.

In addition, the elastic member 563*b* may be provided in one location as illustrated in the drawing, but a plurality of elastic members 563*b* may be provided in a plurality of locations.

Meanwhile, the elastic forces provided to the release member 560 by the elastic member 563*a* of the cartridge 500 according to the first embodiment of the present disclosure and the elastic member 563*b* of the cartridge 500 according to the modification of the first embodiment of the present disclosure need to be greater than the coupling force between the staple 530 and the release member 560. That is, the staple 530, which is fixed to a body tissue during stapling, needs to be released from the release member 560, and thus, the elastic force of the elastic members 563*a* and 563*b* to move the release member 560 downward needs to be greater than the coupling force between the staple 530 and the release member 560.

Second Modification of First Embodiment

Hereinafter, the release member 560 and the staple 530 of the cartridge 500 according to a second modification of the first embodiment of the present disclosure will be described. Here, the cartridge according to the second modification of the first embodiment of the present disclosure is different from the cartridge (see 500 of FIG. 3 and the like) according to the first embodiment of the present disclosure described above, in the shapes of the wedge 541 and the release member 560.

Figure 14A:
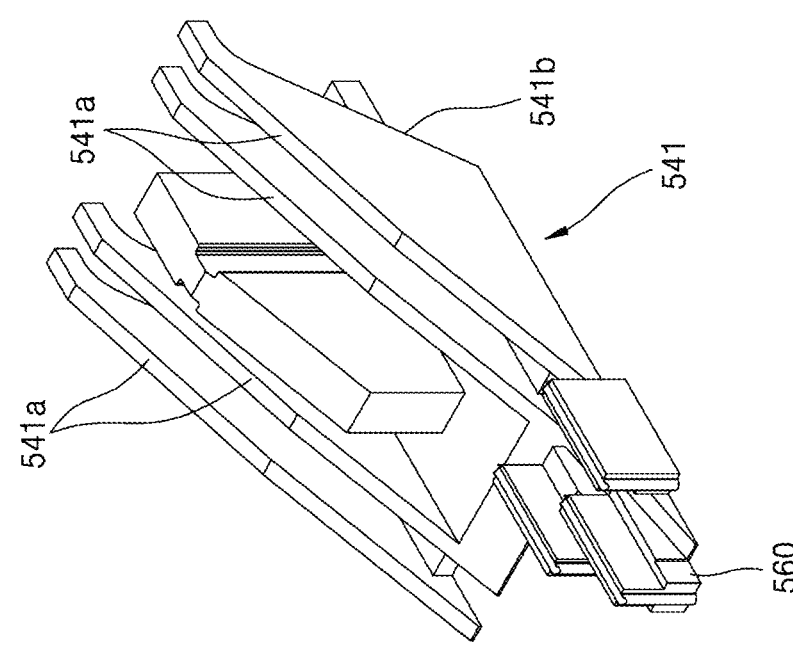
FIGS. 14A and 14B are perspective views illustrating a wedge and a release member of a cartridge for a surgical instrument according to a second modification of the first embodiment of the present disclosure.
Figure 14B:
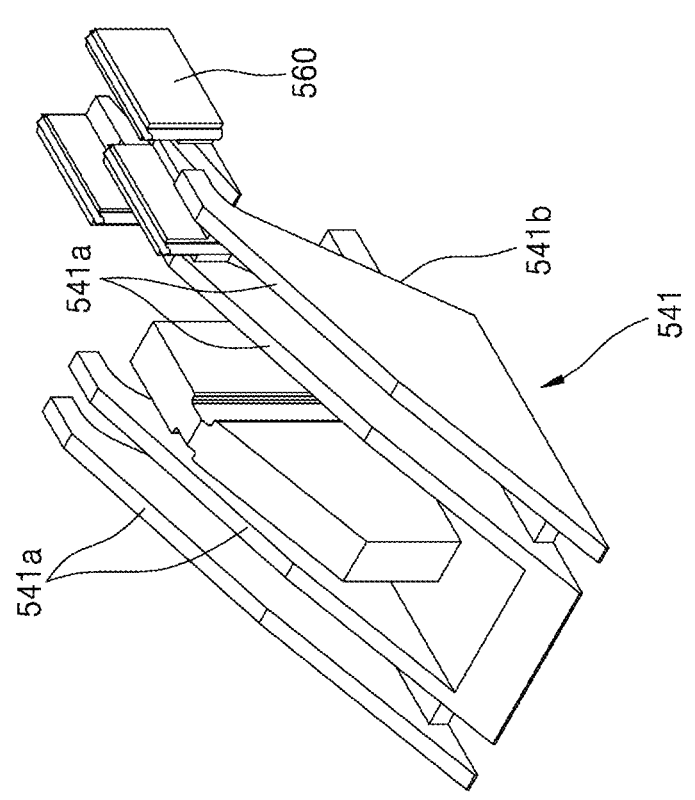
Figure 15:
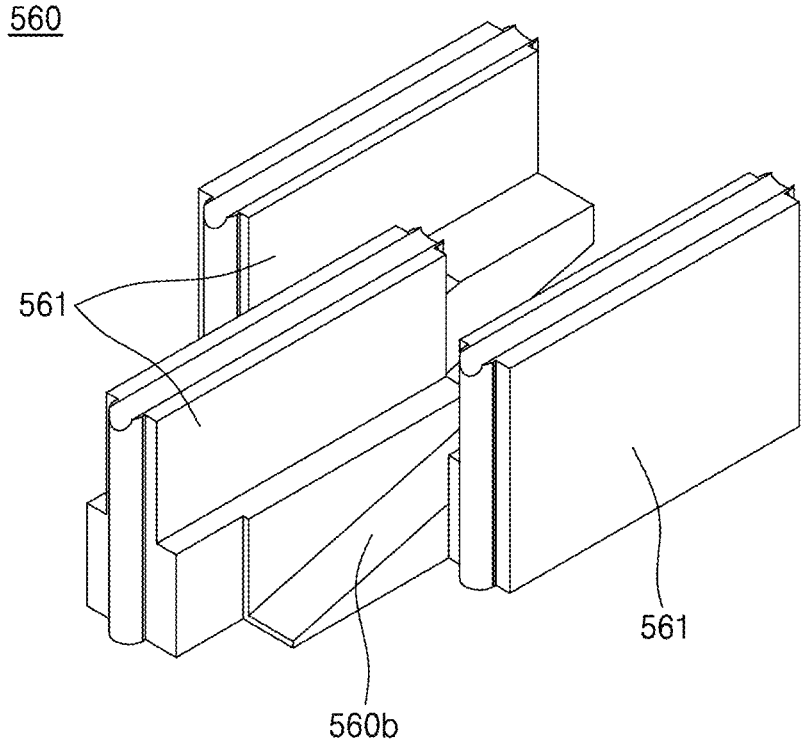
FIGS. 15 and 16 are perspective views illustrating the release member of FIGS. 14A and 14B.
Figure 16:
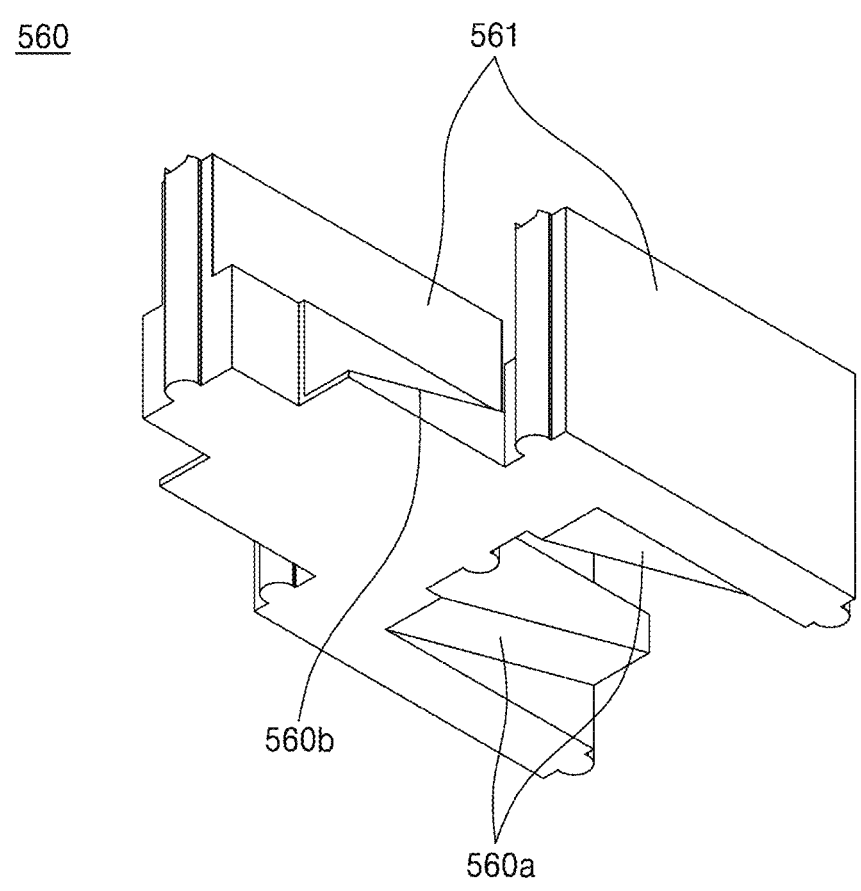

FIGS. 14A and 14B are perspective views illustrating a wedge and a release member of the cartridge of the surgical instrument according to the second modification of the first embodiment of the present disclosure, and FIGS. 15 and 16 are perspective views illustrating the release member of FIGS. 14A and 14B.

Referring to FIGS. 14 to 16, the working member 540 may include the wedge 541 formed on at least one side of the main body (See 545 of FIG. 6), and formed to have a certain inclined surface. That is, the wedge 541 may be formed to be inclined to a certain degree in the extension direction of the connection part 400. In other words, the wedge 541 may include a first inclined surface 541*a* formed such that the height of the first inclined surface 541*a* on the side of the proximal end 501 of the cartridge 500 is higher than the height of the first inclined surface 541*a* on the side of the distal end 502.

In addition, the wedge 541 may include a second inclined surface 541*b* formed from the side of the proximal end of the first inclined surface 541*a*, such that the height of the second inclined surface 541*b* on the side of the distal end is lower than the height of the second inclined surface 541*b* on the side of the proximal end.

That is, when the wedge 541 moves forward from the side of the proximal end 501 of the cartridge 500 toward the side of the distal end 502 in a first direction, which may be defined as the lengthwise direction of the jaw or the lengthwise direction of the cartridge 500, the surface where the wedge 541 comes into contact with the release member 560 may be referred to as the first inclined surface 541*a*. In addition, an inclined surface other than the first inclined surface 541*a* may be formed, and this may be referred to as the second inclined surface 541*b*. Here, the inclination of the second inclined surface 541*b* may be equal to or different from that of the first inclined surface 541*a*.

As a specific example, as illustrated in FIGS. 14A and 14B, the upper starting point of the first inclined surface 541*a* and the upper starting point of the second inclined surface 541$b$ may be close to each other, and the second inclined surface 541$b$ may be formed to be more inclined than the first inclined surface 541$a$.

In addition, when the working member 540 moves toward the distal end 502 of the cartridge 500 in the first direction, the release member 560 may move upward in contact with the first inclined surface 541$a$, and when the working member 540 moves toward the proximal end 501 of the cartridge 500 in the first direction, the release member 560 may move downward in contact with the second inclined surface 541$b$.

In other words, as illustrated in FIG. 14A, when the working member 540 moves forward toward the distal end 502 of the cartridge 500, the release member 560 may slide up the first inclined surface 541$a$. On the contrary, as illustrated in FIG. 14B, when the working member 540 moves backward toward the proximal end 501 of the cartridge 500, the release member 560 may slide down the second inclined surface 541$b$.

Here, the release member 560 may include a first contact surface 560$a$ in contact with the first inclined surface 541$a$ of the wedge 541, and a second contact surface 560$b$ in contact with the second inclined surface 541$b$ of the wedge 541. In addition, the first contact surface 560$a$ and the second contact surface 560$b$ may be inclined surfaces formed to have a height on the side of the proximal end 501 of the cartridge 500 being higher than that on the side of the distal end 502 of the cartridge 500.

In addition, the first contact surface 560$a$ may be formed as an inclined surface having the same inclination as that of the first inclined surface 541$a$. In addition, the second contact surface 560$b$ may be formed as an inclined surface having the same inclination as that of the second inclined surface 541$b$. In addition, the inclinations of the first contact surface 560$a$ and the second contact surface 560$b$ may be equal to or different from each other. That is, the first contact surface 560$a$ may form a certain angle with respect to second contact surface 560$b$.

Here, the first contact surface 560$a$ and the second contact surface 560$b$ may be formed between the supports 561 of the release members 560.

In addition, the first inclined surface 541$a$ of the wedge 541 may be formed as a long and narrow inclined surface, and a pair of first inclined surfaces 541$a$ may be formed to be spaced a certain distance from each other. Similarly, a pair of second inclined surface 541$b$ formed below the first inclined surface 541$a$ may be formed to be spaced a certain distance from each other.

As such, the distance between the wedges 541 may correspond to the thickness of the support 561 of the release member 560, and when the release member 560 slides down in contact with the second inclined surface 541$b$, the support 561 formed at the center of the release member 560 may pass through the gap between the wedges 541. That is, the wedge 541 may serve to guide the release member 560 including the support 561.

As the working member 540 and the wedge 541 move toward the distal end 502 of the cartridge 500, the release member 560 moves upward along the first inclined surface 541$a$ of the wedge 541. Thereafter, when the wedge 541 moves backward toward the proximal end 501 of the cartridge 500, the release member 560 moves downward along the second inclined surface 541$b$. At this time, while the release member 560 is at its highest point after moving upward, the release member 560 may not be in contact with the second inclined surface 541$b$ even through the wedge 541 moves backward, and thus, the release member needs to move downward to a certain degree.

Thus, the cartridge 500 may include the elastic member 563$a$, 563$b$ described above in the first embodiment, such that the release member 560 may move downward to a certain degree from its highest point after moving upward.

However, a body tissue or the staple 530 may act as a kind of spring to move the release member downward. In detail, because the body tissue is interposed between the first jaw 101 and the second jaw 102 and then compressed by the jaws during a stapling process, the body tissue has a force to restore its original thickness. The force acts on the release member 560 protruding above the cover 510 of the cartridge 500, allowing the release member 560 to move downward.

In addition, the staple 530 is deformed into a particular shape as both ends thereof are bent during a stapling process, and at this time, the staple 530 may have a force to return to its original shape. In other words, a spring-back phenomenon may occur during the stapling process. In addition, the force of the staple 530 to return its original shape acts on the release member 560 protruding above the cover 510 of the cartridge 500, allowing the release member 560 to move downward.

As described above, through a process of moving back downward the release member 560, which moved upward during stapling, the staple 530 that is not fixed to a body tissue may be inserted into the cartridge 500 together with the release member 560.

Second Embodiment

Hereinafter, a release member 660 and a staple 630 of a cartridge (not shown) according to a second embodiment of the present disclosure will be described. Here, the cartridge according to the second embodiment of the present disclosure is different from the cartridge (see 500 of FIG. 3 and the like) according to the first embodiment of the present disclosure described above, in the shape of the release member 660.

Figures 17A, 17B:
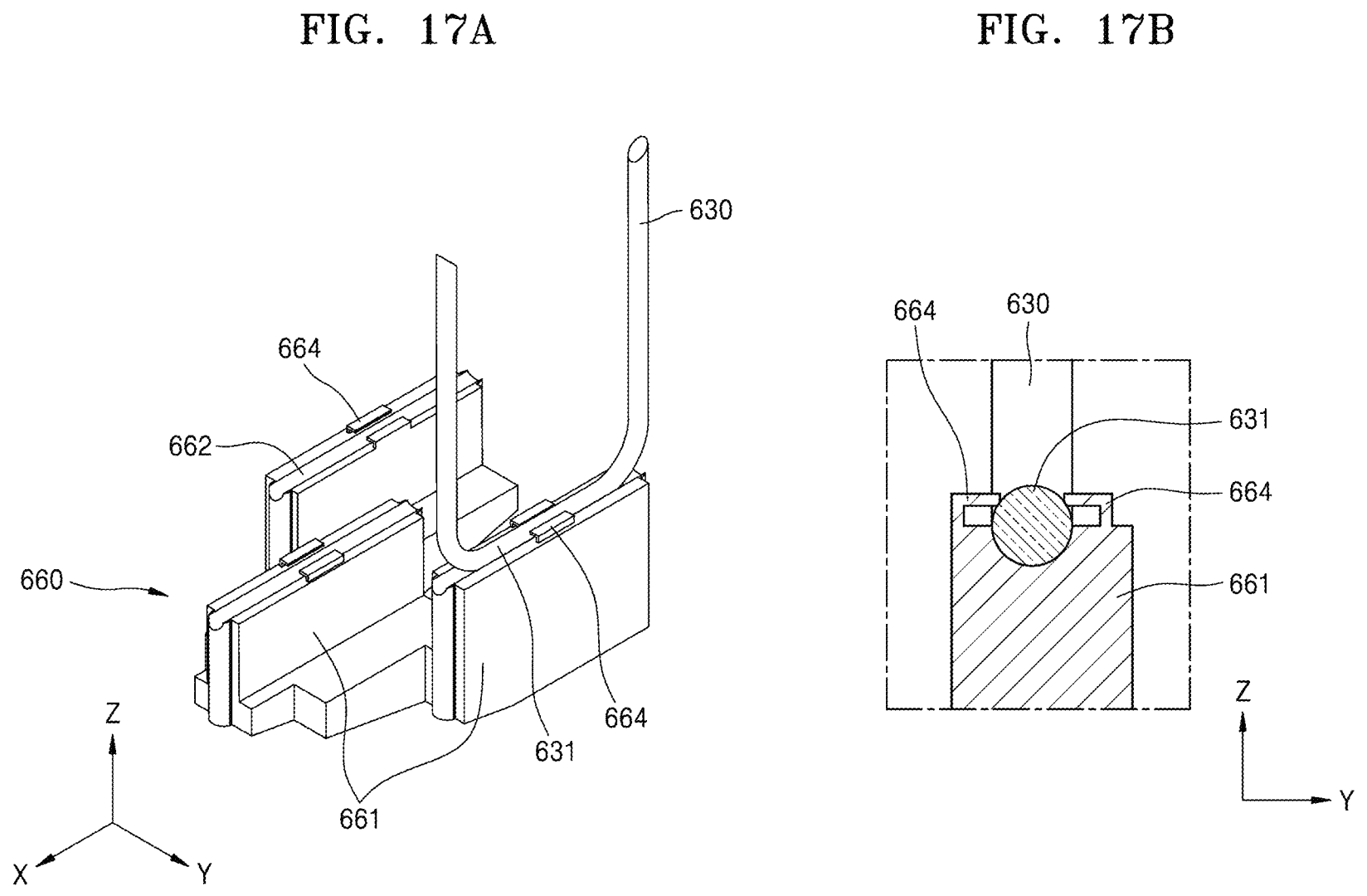

FIG. 17A is a perspective view illustrating a release member and a staple of a cartridge for a surgical instrument according to the second embodiment of the present disclosure. FIG. 17B is a cross-sectional view illustrating a portion of a cross section of the staple and the release member of FIG. 17A.

Referring to FIGS. 17A and 17B, a cartridge (not shown) according to the second embodiment of the present disclosure may include the release member 660 and the staple 630. In addition, although not illustrated in the drawing, the cartridge (not shown) may include a wedge of a working member. The working member, the wedge, and the like are substantially the same as the working member 540 and the wedge 541 of the cartridge 500 according to the first embodiment of the present disclosure, and thus, detailed descriptions thereof will be omitted.

The release member 660 may include a seating part 662 that supports the staple 630 and on which the staple 630 is seated, and the staple 630 may be temporarily fixed to the seating part 662.

Here, the seating part 662 may be formed in a groove shape in the longitudinal direction. In detail, the seating part 662 may be formed as a groove having a shape corresponding to the shape of a lower portion 631 of the staple 630.

There may be various methods of temporarily fixing the staple 630 to the seating part 662 and they will be described below with various embodiments.

For example, the seating part 662 may include one or more fastening members 664.

In detail, the fastening member 664 may be formed in the shape of a hook, and two fastening members 664 may be formed to face each other with the groove of the seating part 662 therebetween. In addition, as illustrated in FIG. 17B, the distance between opposing surfaces of two fastening members 664 may be less than the thickness of the cross section of the lower portion 631 of the staple. That is, when the staple 630 is seated on the seating part 662, the fastening member 664 may interfere with the staple 630. Here, the fastening member 664 may be formed of an elastic member and thus may be elastically deformed such that the staple 630 is seated on the seating part 662. In addition, after the staple 630 is seated on the seating part 662, the staple 630 may be temporarily fixed by the elasticity of the fastening member 664.

The fastening member 664 may be formed with the seating part 662 as one body, or may be formed as a separate member and then coupled to the seating part 662.

As another example of temporarily fixing the staple 630 to the seating part 662, an adhesive may be applied between the seating part 662 of the release member 660 and the staple 630, such that the staple is temporarily fixed to the seating part 662. Here, the adhesive may be a water-soluble adhesive, and when the staple 630 and the release member 660 come into contact with a body tissue, the adhesive may lose its adhesive force due to moisture in the body tissue.

Alternatively, liquid may be applied between the seating part 662 of the release member 660 and the staple 630, such that the staple 630 is temporarily fixed to the seating part 662 by the surface tension of the liquid. Here, the liquid contains moisture or oil, and liquid that does not evaporate may be injected between the seating part 662 and the staple 630 during a manufacturing stage, or a saline solution may be applied to the cartridge before starting a procedure.

As another example, the release member 660 may include a magnetic material and may temporarily fix the staple 630 to the seating part 662 by a magnetic force.

As another example, the seating part 662 of the release member 660 may form a microstructure to temporarily fix the staple 630 to the seating part 662 through an adsorption phenomenon. In detail, a silicone structure with a micropore surface may be formed in the seating part 662. The adsorption phenomenon may weaken over time, but the staple 630 may come into contact with an anvil such that both ends of the staple 630 are bent to apply a pressure to the adsorption structure to restore the adsorption phenomenon.

In a case in which there is only a downward movement structure of the release member 560 as in the cartridge 500 according to the first embodiment of the present disclosure, the release member 560 and the staple 530 may be moved downward together by the gravity, and thus, the floating staple 530 may be retrieved. However, the direction of gravity acting on the staple 530 may change due to the cartridge 500 being tilted, or the staple 530 may collide with the cartridge 500 during a process of retrieving the staple 530, and accordingly, the staple 530 may fail to enter the staple hole 511 and deviate.

Thus, a staple retrieval function may be effectively implemented by adding a structure for fixing the staple 630 to the release member 660 as in the cartridge (not shown) according to the second embodiment of the present disclosure, in addition to the downward movement structure of the release member.

In addition, even only with the temporary fixation characteristics of the release member 660 and the staple 630, when the user retrieves the cartridge (not shown) after stapling, the floating staple 630 may also be retrieved. However, the temporary fixation between several release members 660 and staples 630 is released simultaneously, which may cause strain to body tissues. Thus, it is necessary to appropriately adjust the temporary fixing force between the release member 660 and the staple 630. Here, when the fixing force between the release member 660 and the staple 630 is weak, the temporary fixation may be released with only a slight retraction of the release member 660 by the elasticity of the body tissue and the staple. In addition, even when the staple 630 is not released, the temporary fixing force is weak, and thus, there may be no strain on body tissues when the staple 630 is forcibly released.

First Modification of Second Embodiment

Hereinafter, a release member 760 and a staple 730 of a cartridge (not shown) according to a first modification of the second embodiment of the present disclosure will be described. Here, the cartridge according to the first modification of the second embodiment of the present disclosure is different from the cartridge (see 500 of FIG. 3 and the like) according to the first embodiment of the present disclosure described above, in the shape of the release member 760 or the staple 730.

Figure 18:
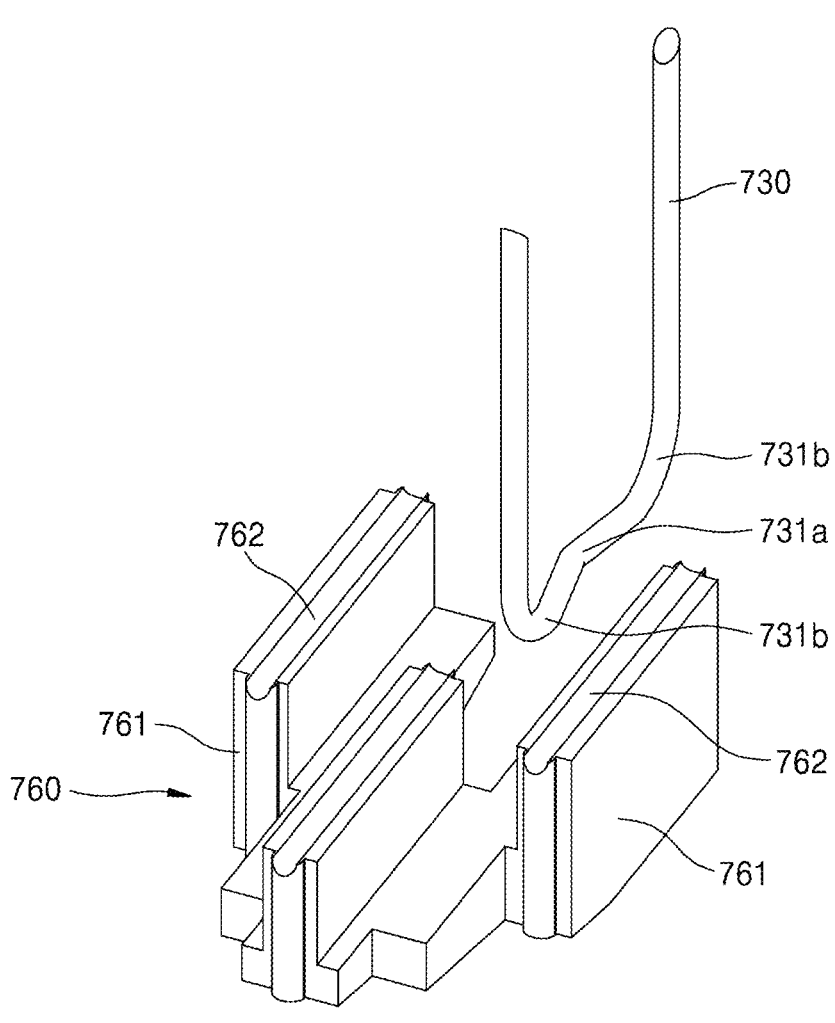
FIG. 18 is a perspective view illustrating a release member and a staple of a cartridge for a surgical instrument according to a first modification of the second embodiment of the present disclosure.

FIG. 18 is a perspective view illustrating a release member and a staple of a cartridge for a surgical instrument according to the first modification of the second embodiment of the present disclosure.

The release member 760 may include a seating part 762, and the seating part 762 may form a groove in the longitudinal direction. A lower portion 731b of the staple 730 seated on the seating part 762 may include a curved section 731a that is laterally curved in at least one area with respect to the longitudinal direction. In addition, when the staple 730 is inserted into the groove of the seating part 762, elastic deformation may occur in the curved section 731a, and the staple 730 may be temporarily fixed to the seating part 762 through the force of the curved section 731a to return to its original state. That is, the curved section 731a of the staple 730 is deformed into a shape close to a straight line so as to be fit into the groove of the seating part 762, but the curved section 731a exerts a force to return to its original curved shape, and thus, an elastic force may be applied to the groove of the seating part 762.

In other words, because the lower portion 731b of the staple 730 is not formed in a straight shape corresponding to the groove of the seating part 762 but a portion of the lower portion 731b is laterally curved, the staple 730 may interfere with the seating part 762 when inserting the staple 730 into the seating part 762. At this time, the staple 730 is elastically deformed and inserted into the groove of the seating part 762, and the elastic force of the staple 730 generates friction between the staple 730 and the seating part 762, allowing the staple 730 and the seating part 762 to be temporarily fixed to each other.

On the contrary, the staple 730 may include the longitudinal lower portion 731b that is seated on the seating part 762, and the seating part 762 may form a groove including a curved section that is laterally curved in at least one area with respect to the longitudinal direction. In addition, when the staple 730 is inserted into the groove of the seating part 762, elastic deformation may occur in the lower portion 731b of the staple 730, and the staple 730 may be temporarily fixed to the seating part 762 through the force of the lower portion 731b to return to its original state. That is, the straight lower portion 731*b* is bent laterally to be fit into the groove of the seating part 762, but the lower portion 731*b* exerts a force to return to its original straight shape, and thus, an elastic force may be applied to the groove of the seating part 762.

In other words, because the lower portion 731*b* of the staple 730 is not formed in a curved shape corresponding to the groove of the seating part 762 but the entire lower portion 731*b* is formed in the shape of a straight line, the staple 730 may interfere with the seating part 762 when inserting the staple 730 into the seating part 762. At this time, the staple 730 is elastically deformed and inserted into the groove of the seating part 762, and the elastic force of the staple 730 generates friction between the staple 730 and the seating part 762, allowing the staple 730 and the seating part 762 to be temporarily fixed to each other.

Second Modification of Second Embodiment

Hereinafter, a release member 860 and a staple 830 of a cartridge 800 according to a second modification of the second embodiment of the present disclosure will be described. Here, the cartridge 800 according to the second modification of the second embodiment of the present disclosure is different from the cartridge (see 500 of FIG. 3 and the like) according to the first embodiment of the present disclosure described above, in the shapes of a housing 820, a cover 810, and the release member 860.

Figure 19:
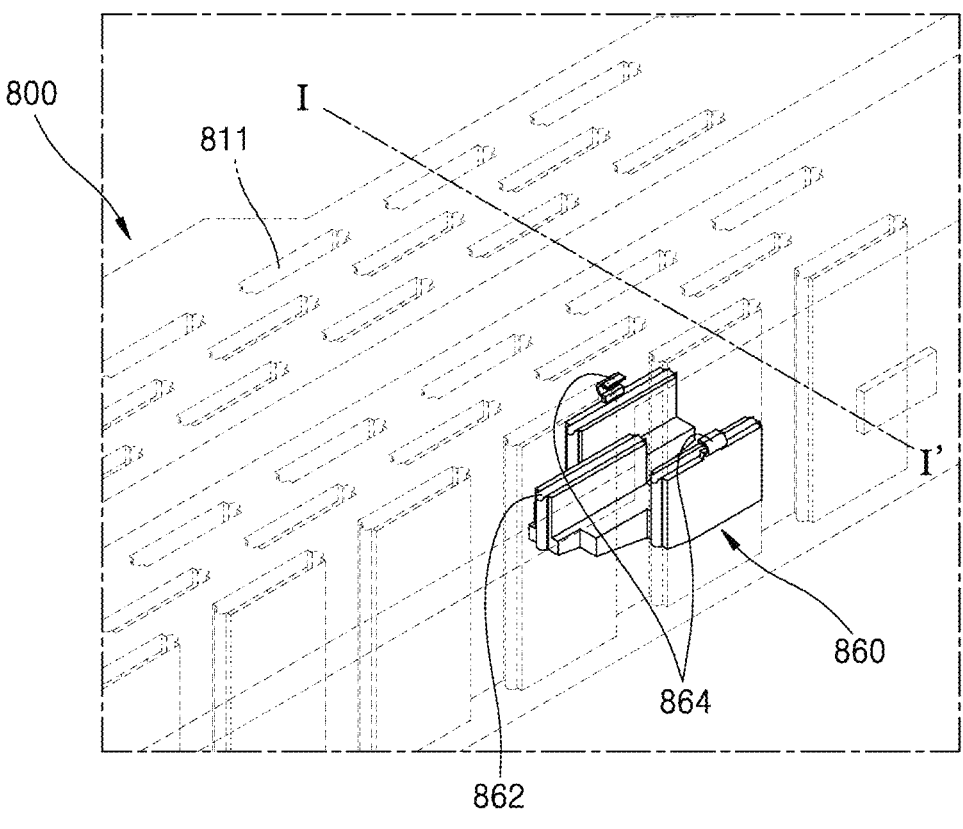
FIG. 19 is a perspective view illustrating a cartridge and a release member of a surgical instrument according to a second modification of the second embodiment of the present disclosure.
Figure 19:
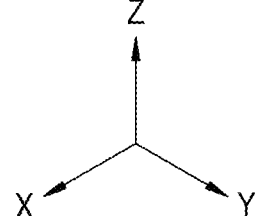
Figure 20:
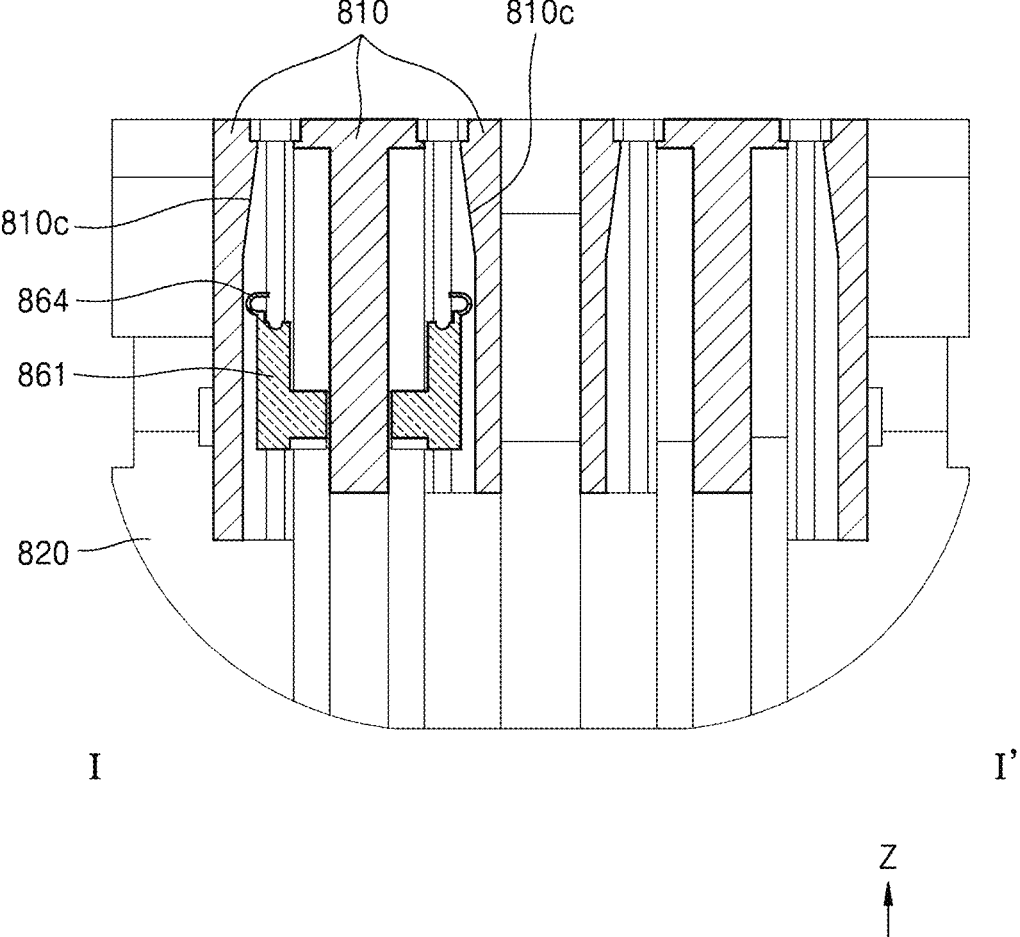
FIG. 20 is a cross-sectional view taken along line I-I' of FIG. 19.

FIG. 19 is a perspective view illustrating a cartridge and a release member of a surgical instrument according to the second modification of the second embodiment of the present disclosure, and FIG. 20 is a cross-sectional view taken along line I-I' of FIG. 19.

Referring to FIGS. 19 and 20, the cartridge 800 according to the second modification of the second embodiment of the present disclosure includes the cover 810, the housing 820, and the release member 860, and although not illustrated in the drawings, may include a working member, a wedge, and the like. The working member, the wedge, and the like are substantially the same as the working member 540 and the wedge 541 of the cartridge 500 according to the first embodiment of the present disclosure, and thus, detailed descriptions thereof will be omitted.

The release member 860 may include a main body support 861 and a seating part 862. The seating part 862 may include a fastening member 864 deformable by an external force, and as the release member 860 moves, the fastening member 864 may be deformed to be fastened to the staple (see 630 of FIG. 17A) such that the staple is temporarily fixed to the seating part.

That is, the fastening member 864 is not fastened to the staple in an initial stage, but may be deformed by an external force to be fastened to the staple. In detail, a portion of the fastening member 864 connected to the seating part 862 may be formed to be easily elastically deformed and to be bent or folded by an external force.

Here, the fastening member 864 may be formed in a similar shape to the fastening member 664 of the release member 660 of the cartridge according to the second embodiment of the present disclosure. In other words, the fastening member 864 may be formed in a hook shape to be easily fastened to a lower portion of the staple.

In addition, a staple hole 811 of the cover 810 may have an inclined surface 810*c* formed such that the inner width of the staple hole 811 becomes narrower toward the upper end of the staple hole 811 than toward the lower end of the staple hole 811. In addition, as the release member 860 moves upward, the fastening member 864 may come into contact with the inclined surface 810*c* and may be deformed by an external force caused by the inclined surface 810*c*.

In other words, a lower portion of the staple hole 811 is formed to be wide enough not to contact the fastening member 864, such that the fastening member 864 is not in contact with the inner wall of the staple hole 811 before the release member 860 moves upward, whereas an upper portion of the staple hole 811 is formed to be narrow enough to contact the fastening member 864 or the support 861, such that the release member 860 comes into contact with the inclined surface 810*c* of the staple hole 811 as the release member 860 moves upward along the staple hole 811.

In addition, it is needless to say that, although the fastening member 864 is in contact with the inner wall of the staple hole 811 before the release member 860 moves upward, an external force sufficient to deform the fastening member 864 is not applied to the fastening member 864, and as the release member 860 moves upward along the staple hole 811, the fastening member 864 may be deformed by receiving an external force from the inclined surface 810*c*.

Alternatively, in a state in which the staple is fixed to the fastening member 864, the fastening member 864 may come into contact with the inner wall of the staple hole 811 and thus be partially deformed, such that the staple is seated in the groove of the seating part 862.

Alternatively, the fastening member 864 may be formed in the same shape as the fastening member 664 illustrated in FIG. 17A. That is, the fastening member 864 may be formed of an elastic material in the shape of a hook, and two fastening members 864 may be formed to face each other with the groove of the seating part 862 therebetween. Here, the staple (see 630 of FIG. 17A) may not be fastened to the fastening member 864, but may be simply placed on the fastening member 864. Then, the release member 860 may move upward along the staple hole 811, the fastening member 864 may be elastically deformed by the force of the staple colliding with a body tissue or an anvil, and eventually, the staple may be fastened to the fastening member 864.

Meanwhile, in a case in which the process of fastening the staple to the fastening member is performed separately in advance, the thin and weak staple may be deformed, and in the above structure, the staple is automatically fastened to the fastening member during a stapling motion, and thus, deformation of the staple that may occur during the separate process of fastening the staple may be prevented.

Third Embodiment

Hereinafter, a cover 910 of a cartridge 900 according to a third embodiment of the present disclosure will be described. Here, the cartridge 900 according to the third embodiment of the present disclosure is different from the cartridge (see 500 of FIG. 3 and the like) according to the first embodiment of the present disclosure described above, in the shape of a staple hole 911 of the cover 910.

Figure 21:
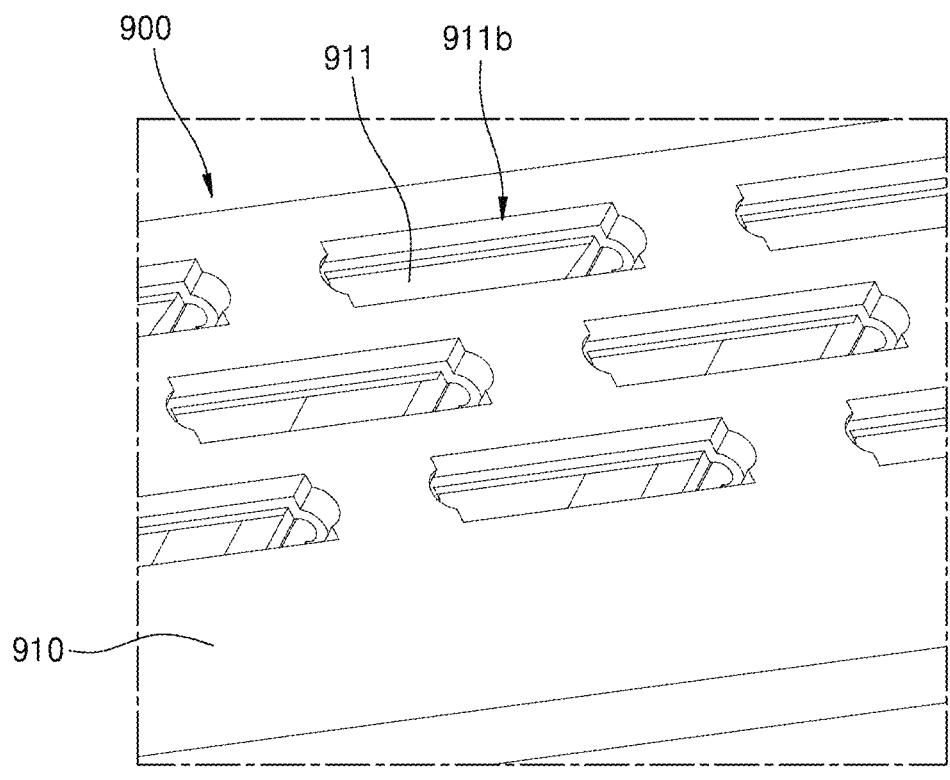
FIG. 21 is an enlarged perspective view illustrating a cartridge for a surgical instrument according to a third embodiment of the present disclosure.
Figure 22:
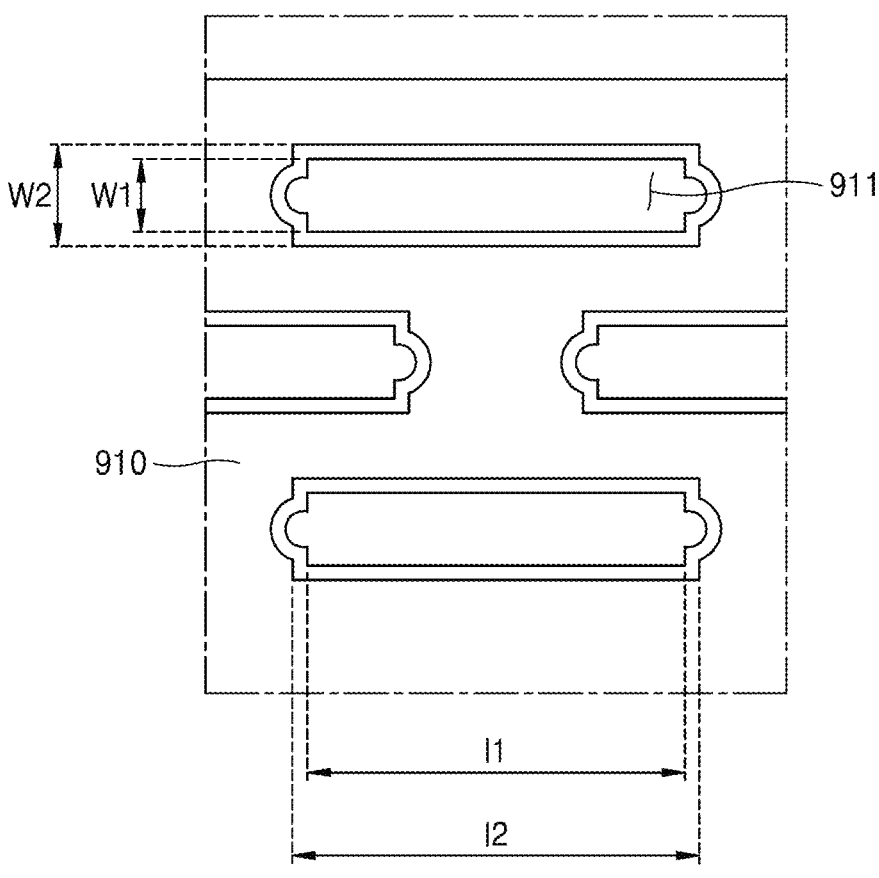
FIG. 22 is a plan view illustrating a cover of the cartridge of FIG. 21.

FIG. 21 is an enlarged perspective view illustrating a cartridge for a surgical instrument according to the third embodiment of the present disclosure, and FIG. 22 is a plan view illustrating a cover of the cartridge of FIG. 21.

Referring to FIGS. 21 and 22, the cartridge 900 according to the third embodiment of the present disclosure may include the cover 910, and the cover 910 may include a plurality of staple holes 911.

The staple hole 911 of the cover 910 may form a pocket 911*b* for accommodating a staple, in an area adjacent to the entrance thereof. Here, the pocket 911*b* may have a width or length greater than that of the staple hole 911, or may have a width and length greater than those of the staple hole 911, and may be formed to have a preset depth.

The staple hole 911 formed in the lengthwise direction of the cartridge 900 is formed in the shape of a slot, and as illustrated in the drawings, a length 12 of the pocket 911b may be greater than a length 11 of the staple hole 911, and a width w2 of the pocket 911b may be greater than a width w1 of the staple hole 911.

Meanwhile, when implementing functions such as the above-described downward movement structure of the release member 560 or the fixed-coupling structure of the staple 530 and the release member 560, the staple 530 that is not fixed to a body tissue will be inserted back into the staple hole 511 of the cartridge 500, but the staple 530, which is already in contact with the anvil such that both ends of the staple 530 are bent, may not be introduced back into the staple hole 511. In this case, the cartridge cover 510 and the staple 530 may collide with each other and the temporary fixation between the staple 530 and the release member 560 may be released, causing the staple 530 to float.

However, in the cartridge 900 according to the third embodiment of the present disclosure, the pocket 911b is formed to be wider than the staple hole 911, and thus, the staple 530, which has failed in stapling and has been released from the release member 560, may be accommodated in the pocket 911b.

It is needless to say that the embodiments or modifications described above may be implemented independently of each other or together with each other.

The present disclosure has been described with reference to the preferred embodiments. It will be understood by those of skill in the art that the present disclosure may be implemented in a modified form without departing from the intrinsic characteristics of the present disclosure. Therefore, the disclosed embodiments are to be considered in a descriptive sense only, and not for purposes of limitation. The scope of the present disclosure is in the claims rather than the above descriptions, and all differences within the equivalent scope should be construed as being included in the present disclosure.

According to the present disclosure, it is possible to automatically retrieve staples that are not fixed to body tissues and are floating during a stapling procedure using a surgical instrument, thereby improving an operator's convenience, and the safety, reliability, and speed of surgery.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

What is claimed is:

1. A cartridge for a surgical instrument having an end tool rotatable in at least one direction, the cartridge comprising:
   a housing;
   a cover covering one surface of the housing and having thereon a staple hole defined to eject therethrough at least one staple accommodated in the housing to an outside;

a working member arranged inside the housing and configured to move relative to the housing in a first direction that is a lengthwise direction of the housing;
   a release member comprising a plurality of supports on which the at least one staple is arranged, wherein, as the working member moves, the release member is configured to move upward from a lower portion of the housing to an upper portion of the housing to eject the at least one staple to the outside; and
   an elastic member arranged between the housing and the cover, the elastic member being configured to provide an elastic force in a direction in which the release member is moved downward,
   wherein the working member comprises one or more wedges, each having a first inclined surface and a second inclined surface configured to be in contact with the release member,
   wherein a height of the first inclined surface on a side of a proximal end of the cartridge is greater than a height of the first inclined surface on a side of a distal end of the cartridge,
   wherein the second inclined surface is defined opposite the first inclined surface, starting from a side of a proximal end of the first inclined surface,
   wherein a height of the second inclined surface on the side of the distal end of the cartridge is lower than a height on the side of the proximal end of the cartridge,
   wherein the release member further comprises:
      a first contact surface formed between the plurality of supports and configured to be in contact with the first inclined surface, and
      a second contact surface defined opposite the first contact surface and configured to be in contact with the second inclined surface, and
   wherein heights of the first contact surface and the second contact surface on the side of the proximal end of the cartridge are greater than heights of the first contact surface and the second contact surface on the side of the distal end of the cartridge.

2. The cartridge of claim 1, wherein the elastic member is fixedly coupled to the release member.

3. The cartridge of claim 2, wherein,
   when the release member moves upward to the upper portion of the housing, the elastic member is configured to be compressed by the cover or an external structure, the elastic member being configured to provide the elastic force in the direction in which the release member is moved downward.

4. The cartridge of claim 1, wherein
   the elastic member is fixedly coupled to the cover, and
   when the release member moves upward to the upper portion of the housing, the elastic member is configured to be compressed by the release member and provide the elastic force in the direction in which the release member is moved downward.

5. The cartridge of claim 1, wherein
   one end of the elastic member is fixedly coupled to the release member, another end of the elastic member is fixedly coupled to the housing, and
   when the release member moves upward, the elastic member stretches and provides an elastic force that returns the release member in a downward direction.

6. The cartridge of claim 1, wherein the elastic force provided by the elastic member to the release member is stronger than a coupling force between the at least one staple and the release member.

7. The cartridge of claim 1, wherein the elastic member and the release member form one body.

8. The cartridge of claim 1, wherein the elastic member is disposed as a separate member from the release member and coupled to the release member.

9. The cartridge of claim 1, wherein, when the working member moves toward the distal end of the cartridge in the first direction, the release member is to come into contact with the first inclined surface and move upward, and when the working member moves toward the proximal end of the cartridge in a direction opposite to the first direction, the release member is to come into contact with the second inclined surface and move downward.

10. The cartridge of claim 1, wherein, as the working member moves toward the distal end of the cartridge in the first direction:

the one or more wedges of the working member are configured to sequentially push up a plurality of staples in the cartridge to perform a stapling motion, and a blade is configured to simultaneously move toward the distal end of the cartridge in the first direction to perform a cutting motion.

11. The cartridge of claim 1, wherein the staple hole of the cover forms a pocket to accommodate the at least one staple, in an area adjacent to an entrance of the staple hole.

12. The cartridge of claim 11, wherein the pocket has a width greater than a width of the staple hole, the pocket having a preset depth.

13. The cartridge of claim 11, wherein the pocket is configured to accommodate the at least one staple that has failed in stapling and has been released from the release member.

14. The cartridge of claim 1, wherein the first inclined surface and the second inclined surface are integrally formed as opposing surfaces on each of the one or more wedges.

15. The cartridge of claim 1, wherein the first contact surface and the second contact surface are integrally formed as opposing surfaces on the release member.

\* \* \* \* \*